(12) United States Patent
Ylitalo et al.

(10) Patent No.: US 8,318,282 B2
(45) Date of Patent: Nov. 27, 2012

(54) MICROSTRUCTURED ANTIMICROBIAL FILM

(75) Inventors: Caroline M. Ylitalo, Stillwater, MN (US); Paul D. Graham, Woodbury, MN (US); Linda K. M. Olson, St. Paul, MN (US); Narina Y. Stepanova, Inver Grove Heights, MN (US); Robin E. Wright, Inver Grove Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 249 days.

(21) Appl. No.: 12/746,792

(22) PCT Filed: Dec. 8, 2008

(86) PCT No.: PCT/US2008/085814
§ 371 (c)(1),
(2), (4) Date: Jun. 8, 2010

(87) PCT Pub. No.: WO2009/076270
PCT Pub. Date: Jun. 18, 2009

(65) Prior Publication Data
US 2010/0263793 A1 Oct. 21, 2010

Related U.S. Application Data

(60) Provisional application No. 61/013,085, filed on Dec. 12, 2007, provisional application No. 61/013,300, filed on Dec. 12, 2007, provisional application No. 61/015,255, filed on Dec. 20, 2007.

(51) Int. Cl.
*B32B 3/30* (2006.01)
*B32B 43/00* (2006.01)

(52) U.S. Cl. ............... 428/43; 428/44; 428/98; 428/156
(58) Field of Classification Search ............. 428/43, 428/44, 98, 156; 435/287.2
See application file for complete search history.

(56) References Cited

U.S. PATENT DOCUMENTS

| | | |
|---|---|---|
| 3,691,140 A | 9/1972 | Silver |
| 3,857,731 A | 12/1974 | Merrill, Jr. et al. |
| 4,166,152 A | 8/1979 | Baker et al. |
| 4,597,975 A | 7/1986 | Woodward et al. |
| 5,454,886 A | 10/1995 | Burrell et al. |
| 5,460,802 A | 10/1995 | Asami et al. |

(Continued)

FOREIGN PATENT DOCUMENTS

CA 1 270 192 6/1990

(Continued)

*Primary Examiner* — Brent O'Hern
(74) *Attorney, Agent, or Firm* — Nicole J. Einerson

(57) ABSTRACT

A microstructured antimicrobial film, an antimicrobial film assembly, a method of protecting a surface from microbial contamination, and a method of making a microstructured antimicrobial film. The microstructured antimicrobial film can include a substrate having a first side that includes a first major surface, a plurality of microstructured wells defined in the first side of the substrate, and an antimicrobial material positioned within at least some of the plurality of wells. Each of the plurality of wells can be at least partially defined by a base that is spaced a distance from the first major surface of the substrate. The antimicrobial material can be positioned, such that an upper surface of the antimicrobial material is spaced a distance from the first major surface of the substrate. The antimicrobial film assembly can include a roll or a stack of microstructured antimicrobial films.

19 Claims, 5 Drawing Sheets

U.S. PATENT DOCUMENTS

| | | | |
|---|---|---|---|
| 5,460,833 A | 10/1995 | Andrews et al. | |
| 5,470,585 A | 11/1995 | Gilchrist | |
| 5,569,461 A | 10/1996 | Andrews | |
| 5,571,617 A | 11/1996 | Cooprider et al. | |
| 5,667,303 A | 9/1997 | Arens et al. | |
| 5,681,575 A | 10/1997 | Burrell et al. | |
| 5,695,857 A | 12/1997 | Burrell et al. | |
| 5,753,251 A | 5/1998 | Burrell et al. | |
| 5,770,255 A | 6/1998 | Burrell et al. | |
| 5,817,325 A | 10/1998 | Sawan et al. | |
| 5,837,275 A | 11/1998 | Burrell et al. | |
| 5,849,311 A | 12/1998 | Sawan et al. | |
| 5,929,160 A | 7/1999 | Krepski et al. | |
| 5,951,993 A | 9/1999 | Scholz et al. | |
| 5,958,440 A | 9/1999 | Burrell et al. | |
| 5,985,308 A | 11/1999 | Burrell et al. | |
| 6,017,553 A | 1/2000 | Burrell et al. | |
| 6,080,490 A | 6/2000 | Burrell et al. | |
| 6,126,931 A | 10/2000 | Sawan et al. | |
| 6,197,814 B1 | 3/2001 | Arata | |
| 6,238,686 B1 | 5/2001 | Burrell et al. | |
| 6,264,936 B1 | 7/2001 | Sawan et al. | |
| 6,267,590 B1 | 7/2001 | Barry et al. | |
| 6,296,863 B1 | 10/2001 | Trogolo et al. | |
| 6,306,419 B1 | 10/2001 | Vachon et al. | |
| 6,333,093 B1 | 12/2001 | Burrell et al. | |
| 6,342,212 B1 | 1/2002 | Schuette et al. | |
| 6,365,130 B1 | 4/2002 | Barry et al. | |
| 6,386,699 B1 | 5/2002 | Ylitalo et al. | |
| 6,420,622 B1 | 7/2002 | Johnston et al. | |
| 6,454,813 B1 | 9/2002 | Chan | |
| 6,462,127 B1 | 10/2002 | Ingrisch et al. | |
| 6,544,621 B1 | 4/2003 | Schuette et al. | |
| 6,582,715 B1 | 6/2003 | Barry et al. | |
| 6,583,176 B2 | 6/2003 | Arata | |
| 6,584,668 B2 | 7/2003 | Green et al. | |
| 6,641,829 B1 | 11/2003 | Green et al. | |
| 6,741,523 B1 | 5/2004 | Bommarito et al. | |
| 6,867,342 B2 | 3/2005 | Johnston et al. | |
| 6,911,243 B2 | 6/2005 | Sher et al. | |
| 7,223,364 B1 | 5/2007 | Johnston et al. | |
| 2002/0082540 A1 | 6/2002 | Johnston et al. | |
| 2002/0128578 A1 | 9/2002 | Johnston et al. | |
| 2003/0199632 A1 | 10/2003 | Mazanek et al. | |
| 2003/0235677 A1 | 12/2003 | Hanschen et al. | |
| 2005/0000642 A1 | 1/2005 | Everaerts et al. | |
| 2005/0089539 A1 | 4/2005 | Scholz et al. | |
| 2005/0129937 A1 | 6/2005 | Patton et al. | |
| 2005/0249791 A1 | 11/2005 | Hobbs et al. | |
| 2006/0012936 A1 | 1/2006 | Choi | |
| 2007/0134784 A1* | 6/2007 | Halverson et al. | 435/287.2 |
| 2007/0196601 A1 | 8/2007 | Ray et al. | |
| 2007/0212266 A1 | 9/2007 | Johnston et al. | |

FOREIGN PATENT DOCUMENTS

| | | |
|---|---|---|
| EP | 0875146 | 11/1998 |
| JP | 11-092305 | 6/1999 |
| WO | WO 00/71183 | 11/2000 |
| WO | WO 00/73082 | 12/2000 |
| WO | WO 00/73083 | 12/2000 |
| WO | WO 01/43549 | 6/2001 |
| WO | WO 01/80920 | 11/2001 |
| WO | WO 04/000568 | 12/2003 |
| WO | WO 04/000569 | 12/2003 |
| WO | WO 2004/039683 | 5/2004 |
| WO | WO 2007/070310 | 6/2007 |
| WO | WO 2007/070650 | 6/2007 |
| WO | WO 2009/076267 | 6/2009 |
| WO | WO 2009/076572 | 6/2009 |

* cited by examiner

MICROSTRUCTURED ANTIMICROBIAL FILM

CROSS REFERENCE TO RELATED APPLICATIONS

This is a national stage filing under 35 U.S.C. 371 of PCT/US2008/085814, filed Dec. 8, 2008, which claims priority to U.S. Provisional Application Nos. 61/013,085, filed Dec. 12, 2007; 61/013,300, filed Dec. 12, 2007; and 61/015,255, filed Dec. 20, 2007; each of which is incorporated herein by reference in its entirety.

FIELD OF THE INVENTION

The present disclosure generally relates to antimicrobial films, and particularly, to microstructured antimicrobial films and assemblies of such microstructured antimicrobial films.

BACKGROUND

Contamination by microorganisms (or microbes) can have dramatic impact on human life and health. Particularly, microbial contamination of food or environmental surfaces may cause morbidity, mortality, decreased worker productivity, and increased health care costs. Contamination can occur in food or on a variety of environmental surfaces and may be due to one or more types of microorganisms, some of which may be pathogens. Foods grown, purchased and consumed by the general population may contain or acquire microorganisms, which can flourish or grow as a function of the environment in which they are located, stored or packaged. This growth may lead to accelerated spoilage of the food product or to the proliferation of pathogenic organisms, which may produce toxins or multiply to infective doses. Because more than one person may come into contact with an environmental surface before it is cleaned or disinfected, a contaminated environmental surface can facilitate the spread of microorganisms.

SUMMARY

To counter the spread of undesired microorganisms, frequently contacted, potentially contaminated surfaces can be cleaned and sanitized on a regular basis. While this provides an immediate reduction in the concentration of microorganisms on given surfaces, the surfaces generally need to be repeatedly cleaned and sanitized on a frequent basis to continue to prevent contamination by microorganisms. Another way to counter contamination and/or proliferation is to implement hygiene practices that render potentially harmful microbes inactive. However, many of such hygiene practices, such as hand washing and/or usage of antimicrobial wipes, sprays or gels, generally need to be performed regularly to be effective, and, as a consequence, may have limited effectiveness due to poor user compliance.

Some embodiments of the present disclosure provide a microstructured antimicrobial film. The microstructured antimicrobial film can include a substrate having a first side, the first side including a first major surface, and a plurality of microstructured wells defined in the first side of the substrate. Each of the plurality of wells can be at least partially defined by a base, which can be spaced a distance from the first major surface of the substrate. Each of the plurality of wells can include at least one dimension in the plane of the first major surface, and the at least one dimension can be less than 1000 micrometers. The microstructured antimicrobial film can further include an antimicrobial material positioned within at least some of the plurality of wells, such that the antimicrobial material has an upper surface that is spaced a distance from the first major surface of the substrate.

Some embodiments of the present disclosure provide a microstructured antimicrobial film. The film can include a substrate having a first side, the first side including a first major surface at least partially defined by the upper surfaces of a plurality of intersecting walls, and a plurality of microstructured wells defined in the first side of the substrate. Each of the plurality of wells can be at least partially defined by a base and at least three of the plurality of intersecting walls, and the base can be spaced a distance from the first major surface of the substrate. Each of the plurality of wells can include at least one dimension in the plane of the first major surface, and the at least one dimension can be less than 1000 micrometers. The microstructured antimicrobial film can further include an antimicrobial material positioned within at least some of the plurality of wells, such that the antimicrobial material has an upper surface that is spaced a distance from the first major surface of the substrate.

Some embodiments of the present disclosure provide an antimicrobial film assembly. The antimicrobial film assembly can include a first antimicrobial film and a second antimicrobial film. Each of the first antimicrobial film and the second antimicrobial film can include a substrate having a first side having a first major surface and a second side having a second major surface, and a plurality of microstructured wells defined in the first side of the substrate. The plurality of wells can be recessed from the first major surface of the substrate. Each of the first antimicrobial film and the second antimicrobial film can further include an antimicrobial material positioned within the plurality of wells. The first antimicrobial film can further include an adhesive coupled to the second major surface of the substrate, and the adhesive of the first antimicrobial film can be positioned in contact with the first major surface of the second antimicrobial film.

Some embodiments of the present disclosure provide a method for protecting a surface from microbial contamination. The method can include providing a first antimicrobial film and a second antimicrobial film. Each of the first antimicrobial film and the second antimicrobial film can include a substrate having a first side having a first major surface and a second side having a second major surface, and a plurality of wells defined in the first side of the substrate, the plurality of wells being recessed from the first major surface. Each of the first antimicrobial film and the second antimicrobial film can further include an antimicrobial material positioned within the plurality of wells, and an adhesive coupled to the second major surface. The adhesive of the first antimicrobial film can be in contact with the first major surface of the second antimicrobial film, and the adhesive of the second antimicrobial film can be coupled to the surface to be protected. The method can further include removing the first antimicrobial film from the second antimicrobial film by removing the adhesive of the first antimicrobial film from contact with the first major surface of the second antimicrobial film to expose the antimicrobial material of the second antimicrobial film.

Some embodiments of the present disclosure provide a method of making a microstructured antimicrobial film. The method can include providing a microstructured antimicrobial film. The microstructured antimicrobial film can include a substrate having a first side, the first side including a first major surface, and a plurality of microstructured wells defined in the first side of the substrate. Each of the plurality of wells can be recessed from the first major surface of the substrate. The method can further include positioning an antimicrobial material within the plurality of microstructured wells, such that the antimicrobial material has an upper surface that is spaced a distance from the first major surface of the substrate.

Other features and aspects of the invention will become apparent by consideration of the detailed description and accompanying drawings.

DETAILED DESCRIPTION

Figure 1:
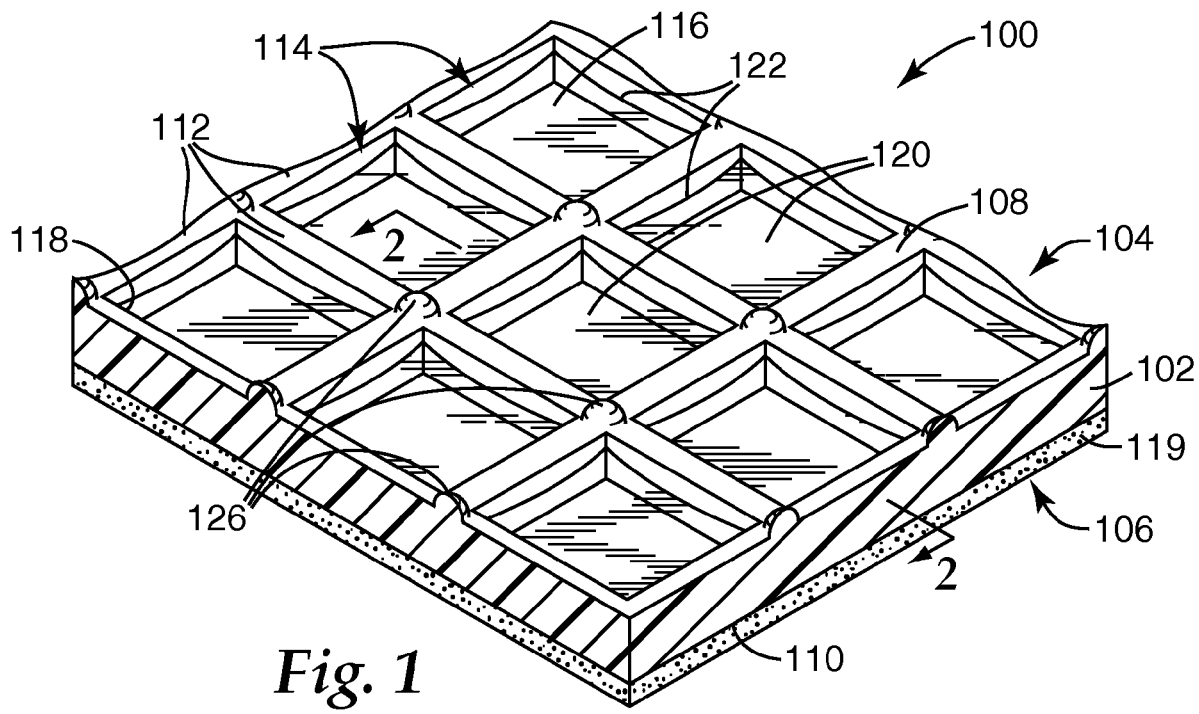
FIG. 1 is a schematic partial perspective view of a microstructured antimicrobial film according to one embodiment of the present disclosure.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompass both direct and indirect couplings. It is to be understood that other embodiments may be utilized, and structural or logical changes may be made without departing from the scope of the present disclosure. Furthermore, terms such as "upper," "lower," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an antimicrobial film, and particularly, to a microstructured antimicrobial film and assemblies of such microstructured antimicrobial films. The present disclosure further relates to a method of making an antimicrobial film and a method of protecting a surface from microbial contamination. The microstructured antimicrobial film, or assemblies of films, of the present disclosure can be used in a variety of applications in which it is desirable to provide antimicrobial activity without transferring antimicrobial material to people, food and/or surfaces that come into contact with the antimicrobial film.

The terms "microorganism," "microbe," or derivatives thereof, are used to refer to any microscopic organism, including without limitation, one or more of bacteria, viruses, algae, fungi and protozoa. In some cases, the microorganisms of particular interest are those that are pathogenic, and the term "pathogen" is used herein to refer to any pathogenic microorganism.

The term "antimicrobial activity" generally includes one or more of (1) killing one or more microorganisms (i.e., providing "biocidal" activity), (2) inhibiting the growth of one or more microorganisms, (3) inhibiting the reproduction of one or more microorganisms, or a combination thereof.

The term "microstructure" or "microstructured feature," and derivatives thereof, is generally used to refer to a structure or a feature having a structure that is a recognizable geometric shape that either protrudes (e.g., a wall) or is depressed (e.g., a well defined at least partially by the wall). For example, a microstructure can include a microstructured well formed to retain a liquid, a solid, a semi-solid, a gelatinous material, another suitable material, or a combination thereof. A microstructure can also include a wall or a base that at least partially defines a microstructured well. Furthermore, a microstructure can include a protrusion, a recess, or the like that is present on any of the above-described microstructures. For example, a microstructured well or wall can be textured, and such textures can also be referred to as microstructures.

The term "microstructured surface" is generally used to refer to a surface that comprises microstructures or microstructured features.

The term "microstructured film" is generally used to refer to a film or other substrate that comprises microstructures or microstructured features. In the present disclosure, the term "microstructured film" generally refers to a film or other substrate that comprises microstructured wells defined in a surface thereof. A microstructured film or substrate can include one or more microstructured surfaces.

The term "microreplicate" and derivatives thereof, is generally used to refer to the production of a microstructured surface through a process where the structured surface features retain an individual feature fidelity during and after manufacture.

The term "primary," when used with reference to a microstructure, is generally used to refer to a microstructure having the largest scale of any microstructure on the same surface.

The term "secondary," when used with reference to a microstructure, is generally used to refer to a microstructure having a smaller scale microstructure relative to one or more primary microstructures on the same surface.

Figure 2:
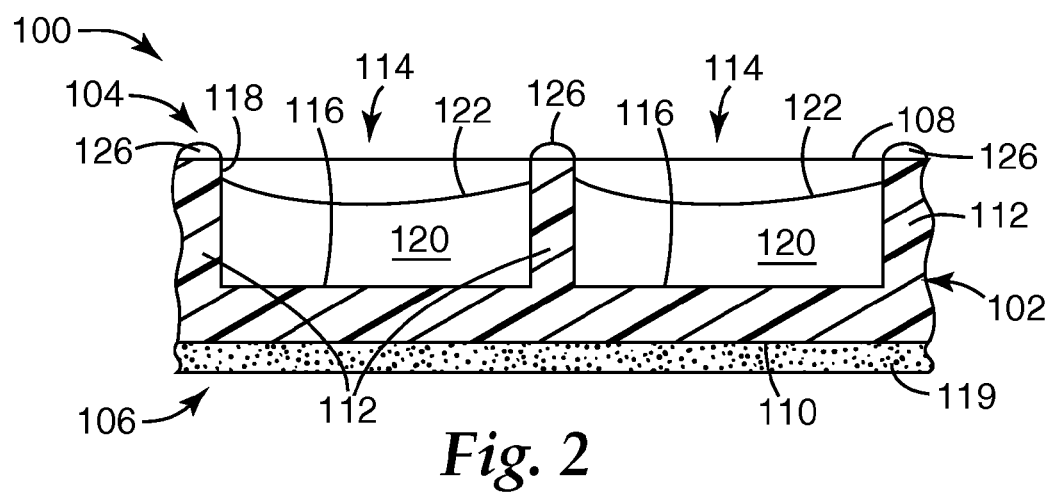
FIG. 2 is a schematic cross-sectional side view of the microstructured antimicrobial film of FIG. 1, taken along line 2-2 in FIG. 1.

FIGS. 1 and 2 illustrate a microstructured antimicrobial film 100 according to one embodiment of the present disclosure. The microstructured antimicrobial film 100 includes a substrate 102 having a first microstructured side 104 and a second side 106. The first side 104 of the substrate 102 includes a first major surface 108, and the second side 106 of the substrate 102 includes second major surface 110. In the embodiment illustrated in FIGS. 1 and 2, the first major surface 108 is defined at least partially by a plurality of intersecting walls 112, and particularly, by an upper surface of the plurality of intersecting walls 112.

The first side 104 of the substrate 102 further includes a plurality of wells 114 that are each defined at least partially by four walls 112 and a base 116. The base 116 is spaced a distance from the first major surface 108 of the substrate 102, such that the wells 114 are recessed in the first side 104 of the substrate 102. The walls 112 and the base 116 at least partially define an inner surface 118 of one well 114, and the inner surface 118 of the well 114 extends inwardly from the first major surface 108 of the substrate 102. The wells 114 can be formed by a variety of processes, including a variety of microreplication processes, which will be described in greater detail below. The first side 104 of the substrate 102 can also be referred to as "the microstructured side" 104 of the substrate 102, and the first major surface 108 of the substrate 102 can also be referred to as "the microstructured surface" 108 of the substrate 102.

The microstructured antimicrobial film 100 further includes an adhesive 119 coupled to the second major surface 110 on the second side 106 of the substrate 102. The adhesive 119 can facilitate coupling the microstructured antimicrobial film 100 to a surface to provide antimicrobial activity to the surface. Positioning the adhesive 119 adjacent the second side 106 of the substrate 102 allows the first side 104 of the substrate 102 to be exposed, or to face away from a surface to which the microstructured antimicrobial film 100 is coupled. The adhesive 119 can be formed of a variety of materials, as described in greater detail below. Some embodiments, however, do not include an adhesive 119. For example, in some embodiments, the microstructured antimicrobial film 100 can be used as a wrap material (e.g. food wrap) and need not include any adhesive. However, in some embodiments, as described in greater detail below, the adhesive 119 can include an electrostatic charge, which can also be useful in wrap materials.

In the embodiment illustrated in FIGS. 1 and 2, the adhesive 119 is a continuous layer coupled to the second side 106 of the substrate 102. However, it should be understood that in some embodiments, the adhesive 119 can be continuous, discrete (e.g. a pattern formed by discrete portions), or a combination thereof.

In some embodiments, the thickness of the microstructured antimicrobial film 100 (including the adhesive 119) can be at least about 50 micrometers, in some embodiments, at least about 500 micrometers, and in some embodiments, at least about 5000 micrometers. In some embodiments, the thickness of the microstructured antimicrobial film 100 can be no greater than about 1000 micrometers, in some embodiments, no greater than about 100 micrometers, and in some embodiments, no greater than about 50 micrometers.

The substrate 102 can be formed of a variety of materials, including metal, polymer, glass, ceramic, other materials amenable to any of the below processing methods, and combinations thereof (e.g., composite materials). Examples of suitable polymeric materials can include, but are not limited to, thermoplastics such as polyolefins (e.g., polypropylene, polyethylene, etc.), polyvinyl chlorides, copolymers of olefins (e.g., copolymers of propylene, etc.), copolymers of ethylene with vinyl acetate or vinyl alcohol, fluorinated thermoplastics such as copolymers and terpolymers of hexafluoropropylene and surface modified versions thereof, polyesters (e.g., polyethylene terephthalate, etc.) and copolymers thereof, polyurethanes, polyimides, poly(meth)acrylates (e.g., polymethyl methacrylate), biodegradable polymers (e.g., a cellulose derivative, polyglycolic acids, polylactic acids, etc.), filled versions of the above, (e.g., using one or more fillers such as silicates, silica, aluminates, feldspar, talc, calcium carbonate, titanium dioxide, etc.), and combinations thereof. Also suitable may be coextruded films and laminated films made from any of the materials listed above. In some embodiments, the microstructured surface 108 includes polyvinyl chloride, polyethylene, polypropylene, or copolymers thereof. The term "(meth)acrylate" generally refers to a methacrylate, an acrylate, or a combination thereof.

In some embodiments, the substrate 102 is gas-permeable, and in some embodiments, the substrate 102 is gas-impermeable. In addition, the substrate 102 can be opaque, translucent, transparent, or a combination thereof (e.g., the substrate 102 can include at least one opaque region, and at least one transparent region), depending on the desired use of the microstructured antimicrobial film 100.

The microstructured surface 108 of the substrate 102 can be formed by a variety of methods, including a variety of microreplication methods, including, but not limited to, casting, coating, and/or compressing techniques. For example, microstructuring of the microstructured surface 108 can be achieved by at least one of (1) casting a molten thermoplastic using a tool having a microstructured pattern, (2) coating of a fluid onto a tool having a microstructured pattern, solidifying the fluid, and removing the resulting film, and/or (3) passing a thermoplastic film through a nip roll to compress against a tool having a microstructured pattern (i.e., embossing). The tool can be formed using any of a number of techniques known to those skilled in the art, selected depending in part upon the tool material and features of the desired topography. Illustrative techniques include etching (e.g., chemical etching, mechanical etching, or other ablative means such as laser ablation or reactive ion etching, etc., and combinations thereof), photolithography, stereolithography, micromachining, knurling (e.g., cutting knurling or acid enhanced knurling), scoring, cutting, etc., or combinations thereof.

Alternative methods of forming the microstructured surface 108 include thermoplastic extrusion, curable fluid coating methods, and embossing thermoplastic layers, which can also be cured. Additional information regarding the substrate material and various processes for forming the microstructured surface 108 of the substrate 102 can be found, for example, in Halverson et al., PCT Publication No. WO 2007/070310, Hanschen et al., US. Publication No. US 2003/0235677, and Graham et al., PCT Publication No. WO 2004/000569.

With microreplication, the microstructured surface 108 can be mass produced without substantial variation from product-to-product and without using relatively complicated processing techniques. In some embodiments, microreplication can produce a microstructured surface that retains an individual feature fidelity during and after manufacture, from product-to-product, that varies by no more than about 50 micrometers. In some embodiments, the microstructured surface 108 retains an individual feature fidelity during and after manufacture, from product-to-product, which varies by no more than 25 micrometers. In some embodiments, the microstructured surface 108 comprises a topography (i.e., the surface features of an object, place or region thereof) that has an individual feature fidelity that is maintained with a resolution of between about 50 micrometers and 0.05 micrometers, and in some embodiments, between about 25 micrometers and 1 micrometer.

In some embodiments, the thickness of the substrate 102 can be at least about 25 micrometers, in some embodiments, at least about 100 micrometers, and in some embodiments, at least about 400 micrometers. In some embodiments, the thickness of the substrate 102 can be no greater than about 2000 micrometers, in some embodiments, no greater than about 1000 micrometers, and in some embodiments, no greater than about 250 micrometers.

The wells 114 are adapted to retain an antimicrobial material 120 in a position that allows the antimicrobial material 120 to be accessible to microbes that come into contact with (or near) the first side 104 of the microstructured antimicrobial film 100, without requiring that the antimicrobial material 120 be present directly on the first major surface 108. The antimicrobial material 120 includes an upper surface 122. In some embodiments, as shown in FIGS. 1 and 2, the antimicrobial material 120 is positioned in the wells 114, such that the antimicrobial material 120 partially fills one or more of the wells 114, and the upper surface 122 of the antimicrobial material 120 is spaced a distance from the first major surface 108 of the substrate 102. As a result, the antimicrobial material 120 is recessed in the first side 104 of the substrate 102. The microstructured antimicrobial film 100, and particularly, the microstructured surface 108, substantially retains its geometry and surface characteristics following manufacture and upon exposure to an antimicrobial material 120.

In some embodiments, the antimicrobial material 120 can also be positioned on the first major surface 108, or a portion thereof. However, the antimicrobial material 120 need not be positioned on the first major surface 108 to be effective in providing antimicrobial activity to microbes that come into contact with (or near) the first side 104 of the microstructured antimicrobial film 100. In addition, if the portion of the antimicrobial material 120 that is present on the first major surface 108 were to be removed from the first major surface 108 (e.g., intentionally or unintentionally, prior to use, during use, during cleaning, or when another microstructured antimicrobial film (or a portion of the same microstructured antimicrobial film, in the case of a roll) is removed from contact therewith), the microstructured antimicrobial film 100 would still retain its antimicrobial activity due to the antimicrobial material 120 positioned in the wells 114 and recessed from the first major surface 108.

The phrase "positioned in/within the wells 114" is meant only to indicate that the antimicrobial material 120 is positioned in one or more of the wells 114, and is not meant to indicate that the antimicrobial material 120 is positioned in all of the wells 114 of the microstructured antimicrobial film 100, or to indicate that the wells 114 that contain the antimicrobial material 120 contain an equal amount of the antimicrobial material 120. Rather, the antimicrobial material 120 can be positioned in particular amounts and/or in particular wells 114 to provide the desired efficacy and potency of antimicrobial activity. In some embodiments, some of the antimicrobial material 120 resides on the inner surface 118 of the well(s) 114.

The antimicrobial material 120 can be positioned in the wells 114 by a variety of methods. Some of the positioning methods include, but are not limited to, a variety of printing methods, a variety of coating methods, gravity filling, pressure filling, vacuum filling, capillary action, or a combination thereof. Examples of printing methods can include, but are not limited to, gravure, off-set, flexographic, lithographic, electrographic, electrophotographic (including laser printing and xerography), ion deposition (also referred to as electron beam imaging (EBI)), magnetographics, inkjet printing, dye sublimation printing, screen printing, and combinations thereof. Examples of coating methods can include, but are not limited to, notch bar coating, rod coating, wire bar coating, spray coating, brushing, controlled orifice die coating, and combinations thereof.

The antimicrobial material 120 can be positioned in at least a portion of the wells 114, such that the antimicrobial material 120 is positioned in at least 5 percent of the volume of the wells 114 in the microstructured surface 108. In some embodiments, the antimicrobial material 120 can be positioned in at least 15 percent, in some embodiments, in at least 25 percent, and in some embodiments, at least 35 percent of the volume of the wells 114.

In some embodiments, the antimicrobial material 120 can be positioned in less than 100 percent of the volume of the wells 114 to allow the upper surface 122 of the antimicrobial material 120 to remain spaced a distance from the first major surface 108. In some embodiments, the antimicrobial material 120 can be positioned in less than 90 percent of the volume of the wells 114, in some embodiments, less than 80 percent, in some embodiments, less than 70 percent, and in some embodiments, less than 50 percent of the volume of the wells 114. In some embodiments in which the antimicrobial material 120 is not present in each of the wells 114, the antimicrobial material 120 is positioned in less than 100 percent of the volume of the wells 114 that do contain the antimicrobial material 120. For example, if only 50 percent of the wells 114 in the microstructured antimicrobial film 100 contain antimicrobial material 120, in some embodiments, the antimicrobial material 120 is positioned in less than 100 percent of the volume of those 50 percent of the wells 114 in which the antimicrobial material 120 is present.

Each of the wells 114 are shown in FIGS. 1 and 2 as being formed by four walls 112 and a base 116 by way of example only, and each well 114 is separated from an adjacent well 114 by a wall 112. However, it should be understood that the wells 114 can include a variety of shapes, as long as the wells 114 are defined in the substrate 102 and recessed from the first major surface 108 of the substrate 102 so as to be able to retain the antimicrobial material 120. Said another way, the wells 114 can include a variety of shapes that allow the inner surface 118 of the wells 114 to extend inwardly from the first major surface 108 of the substrate. Each of the wells 114 is shaped and dimensioned to retain the antimicrobial material 120 away from the first major surface 108. That is, each of the wells 114 is shaped and dimensioned to provide a reservoir for the antimicrobial material 120, and is not necessarily designed to promote fluid flow. The microstructured features of the first side 104 of the substrate 102 may facilitate the filling of the wells 114 (e.g., by capillary action) with the antimicrobial material 120. However, after the antimicrobial material 120 has been positioned in the wells 114 of the substrate 102, the wells 114 are not shaped or dimensioned to promote the migration or flow of antimicrobial material 120 from one well 114 to another. For example, in some embodiments, the wells 114 can be defined at least partially by at least three walls 112 (i.e., so as not to form a fluidic channel) and the base 116.

Examples of suitable well shapes include, but are not limited to, a variety of polyhedral shapes, parallelepipeds (e.g., as shown in FIGS. 1 and 2), prismatoids, prismoids, etc., and combinations thereof. For example, the wells 114 can be polyhedral, conical, frusto-conical, pyramidal, frusto-pyramidal, spherical, partially spherical, hemispherical, ellipsoidal, dome-shaped, cube-corner shaped, etc., and combinations thereof. Furthermore, the wells 114 can have a variety of cross-sectional shapes (including a vertical cross-section as shown in FIG. 2, a horizontal cross-section, or a combination thereof), including, but not limited to, at least one of parallelograms, parallelograms with rounded corners, rectangles, squares, circles, half-circles, ellipses, half-ellipses, triangles, trapezoids, stars, other polygons (e.g., having more than four sides), etc., and combinations thereof.

In some embodiments, the wells 114 are shaped to include edges or corners. Such edges or corners can facilitate the retention of the antimicrobial material 120 in the wells 114 and inhibit the antimicrobial material 120 from being removed from the wells 114 during use. For example, in embodiments in which the antimicrobial material 120 has a high surface energy, or in which the antimicrobial material 120 includes molecules that are attracted to those of the substrate material, the antimicrobial material 120 can be preferentially attracted to edges and/or corners of the wells 114 (i.e., where the antimicrobial material 120 can remain in contact with two or more surfaces), rather than smooth single surfaces.

In the embodiment illustrated in FIGS. 1 and 2, the base 116 of each well 114 is flat and planar (i.e., has an area), and is substantially parallel to the first major surface 108 of the substrate 102. However, because other shapes of wells 114 are possible, the base 116 need not be planar, but rather can include a point or a line of the well 114 that is spaced the greatest distance from the first major surface 108 of the substrate 102. For example, in embodiments employing one or more hemispherical wells 114, the base 116 of such wells 114 can include the point in the hemisphere that is spaced the greatest distance from the first major surface 108. In addition, even in embodiments employing a planar base 116, the base 116 need not be flat, but rather can be curved, flat, or a combination thereof. Furthermore, even in embodiments employing a flat, planar base 116, the base 116 need not be parallel to the first major surface 108.

Furthermore, in the embodiment illustrated in FIGS. 1 and 2, the wells 114 are each shown as having various lines of symmetry, and the base 116 is centered with respect to the opening of the well 114. However, it should be understood that the wells 114 need not include any lines of symmetry, and the base 116 (whether the base 116 includes a point, a line or an area) need not be centered with respect to the opening of the well 114.

The wells 114 illustrated in FIGS. 1 and 2 are shown by way of example only as being of the same size and shape; however, it should be understood that all of the wells 114 defined in the first side 104 of the substrate 102 do not need to be of the same size or shape. That is, the wells 114 can all be formed of about the same shape and size, the same or similar shape but different sizes, different shapes but similar sizes, different shapes and sizes, or a combination thereof. For example, in some embodiments, the microstructured side 104 of the substrate 102 can include a pattern of alternating sizes of similarly-shaped wells 114, or regions of wells 114 wherein the wells 114 of one region are of the same size (or shape) but are not of the same size (or shape) as an adjacent region.

Furthermore, the wells 114 illustrated in FIGS. 1 and 2 are shown by way of example only as being regularly arranged in a cellular array. However, it should be understood that the substrate 102 can include a variety of regular arrangements or arrays, random arrangements, or combinations thereof. In some embodiments, the wells 114 are arranged randomly on a local or smaller scale, but the random arrangements repeat, or are ordered, on a larger scale. Alternatively, in some embodiments, the wells 114 are ordered on a smaller scale, but the ordered regions are randomly arranged on a larger scale.

In addition, in the embodiment illustrated in FIGS. 1 and 2, the walls 112 are all of the same size and shape. However, it should be understood that a variety of other wall shapes are possible. For example, the walls 112 need not include a substantially rectangular cross-sectional shape, but rather can include any of the above-described cross-sectional shapes.

The walls 112 and the wells 114 can be characterized by a variety of sizes, dimensions, distances between walls 112 or wells 114, relative sizes, etc. The walls 112 generally have dimensions such as thickness, height, length, width, etc. The wells 114 generally have volumes with dimensions such as a radius, diameter, height, width, length, etc. Generally, the walls 112 and/or the wells 114 are sized, shaped and spaced to retain the antimicrobial material 120 in the wells 114 when the microstructured antimicrobial film 100 is in any orientation (e.g., by capillary forces). In addition, the walls 112 and/or wells 114 are sized, shaped and spaced in a position that allows the antimicrobial material 120 to be recessed from the first major surface 108, while still allowing the antimicrobial material 120 to be positioned at an effective distance from the first major surface 108 to allow the antimicrobial material 120 to provide antimicrobial activity to the first side 104 of the microstructured antimicrobial film 100. In this way, the antimicrobial material 120 can provide antimicrobial activity to the first side 104 of the microstructured antimicrobial film 100 without requiring the antimicrobial material 120 to be present directly on the first major surface 108 (even though, as mentioned above, this may occur in some embodiments). In some embodiments, the walls 112 and/or wells 114 can be sized so as not to be visible to the naked human eye, which can create a more aesthetically pleasing surface and can limit the conspicuity of the microstructured antimicrobial film 100.

By allowing the antimicrobial material 120 to be recessed with respect to the first major surface 108, the microstructured antimicrobial film 100 can be stacked and/or rolled without a release liner. Even if any antimicrobial material 120 is present on the first major surface 108, and is disturbed by the adhesive 119 or second side 106 of an adjacent microstructured antimicrobial film 100, the majority of the antimicrobial material 120 will remain undisturbed within the wells 114 of the microstructured antimicrobial film 100, and the microstructured antimicrobial film 100 will maintain its antimicrobial activity. Such constructions are described in greater detail below.

In some embodiments, the walls 112 can have an average thickness of at least about 1 micrometer, in some embodiments, at least about 5 micrometers, and in some embodiments, at least about 10 micrometers. In some embodiments, the walls 112 can have an average thickness of no greater than about 50 micrometers, in some embodiments, no greater than about 30 micrometers, and in some embodiments, no greater than about 20 micrometers.

In some embodiments, the configuration of the walls 112 and the wells 114 in any given region of the microstructured surface 108 is chosen such that the average wall or well pitch (i.e., the center to center distance between adjacent walls 112 or wells 114, respectively) is at least about 1 micrometer, in some embodiments, at least about 10 micrometers, and in some embodiments, at least about 50 micrometers. In some embodiments, the average well pitch is no greater than about 1000 micrometers, in some embodiments, no greater than about 500 micrometers, and in some embodiments, no greater than about 400 micrometers.

In some embodiments, the wells 114 can be characterized by an x-direction dimension in the plane of the first major surface 108 (e.g., a length, a width, a radius, a diameter, a diagonal, etc.). The phrase "in the plane of" is used to generally refer to an x-y plane dimension, and is only used to distinguish from a depth or a z-direction dimension, but does not require the dimension to be located exactly in the plane of the first major surface 108, but rather can include dimensions that lie in other similar x-y planes that are substantially parallel to the plane of the first major surface 108. In some embodiments, the average well x-direction dimension is at least about 1 micrometer, in some embodiments, at least about 10 micrometers, and in some embodiments, at least about 50 micrometers. In some embodiments, the average well x-direction dimension is less about 1000 micrometers, in some embodiments, less than about 500 micrometers, and in some embodiments, less than about 100 micrometers.

In some embodiments, the average well volume is at least about 1 picoliter (pL), in some embodiments, at least about 3 pL, in some embodiments, at least about 30 pL, and in some embodiments, at least about 300 pL. In some embodiments, the average well volume is no greater than about 20,000 pL, in some embodiments, no greater than about 10,000 pL, and in some embodiments, no greater than about 5,000 pL.

Another way to characterize the walls 112 and the wells 114 is to describe them in terms of their aspect ratios. An "aspect ratio" of a well 114 is the ratio of the depth of a well 114 to the width of the well 114. An "aspect ratio" of a wall 112 is the ratio of the height of the wall 112 to the width (or thickness) of the wall 112. In some embodiments, the average well aspect ratio is at least about 0.01, in some embodiments, at least about 0.05, and in some embodiments, at least about 1. In some embodiments, the average well aspect ratio is no greater than about 2, in some embodiments, no greater than about 1, and in some embodiments, no greater than about 0.8.

In some embodiments, the average wall aspect ratio is at least about 0.01, in some embodiments, at least about 0.05, and in some embodiments, at least about 1. In some embodiments, the average wall aspect ratio is no greater than about 15, in some embodiments, no greater than about 10, and in some embodiments, no greater than about 8.

In some embodiments, the average height of the walls 112 or the average depth of the wells 114 (i.e., the distance between the base 116 of the well 114 and the top of the well 114, i.e., the adjacent portion of the first major surface 108) is at least about 5 micrometers, in some embodiments, at least about 20 micrometers, and in some embodiments, at least about 30 micrometers. In some embodiments, the average height of the walls 112 or the average depth of the wells 114 can be no greater than about 200 micrometers, in some embodiments, no greater than about 100 micrometers, and in some embodiments, no greater than about 50 micrometers. In the embodiment illustrated in FIGS. 1 and 2, the wall height is substantially the same as the well depth; however, it should be understood that this need not be the case. For example, in some embodiments, the wells 114 include a portion that is recessed even below the bottom of the walls 112, such that the well depth is greater than the wall height. However, even in such embodiments, the above size ranges apply.

In some embodiments, such as the embodiment illustrated in FIGS. 1 and 2, the first major surface 108 of the substrate 102 can be further defined by a plurality of protrusions 126 located at each intersection of the walls 112. The protrusions 126 can serve as a point of contact (or line or area of contact, but referred to for simplicity as a "point of contact") between adjacent microstructured antimicrobial films 100, which will be described in greater detail below with reference to FIG. 3. The protrusions 126 are shown as being regularly distributed in the microstructured side 104 of the substrate 102 at each of the intersections of the wall 112. However, it should be understood that the microstructured antimicrobial film 100 can include fewer (e.g., none, in some embodiments) or more of the protrusions 126, and that the protrusions 126 need not be regularly arranged, but rather can be randomly arranged, or can have a combination of regular and random arrangements. In the embodiment illustrated in FIGS. 1 and 2, the protrusions 126 are formed of the same material as the substrate 102 and are formed by the same microreplication process that forms the walls 112 and the wells 114; however, it should be understood that the protrusions 126 can instead be formed of a different material from the substrate 102 and can be formed subsequently to the formation of the other microstructured features in the microstructured antimicrobial film 100. In some embodiments, the microstructured side 104 of the substrate 102 includes additional microstructured features, which can include additional protrusions, depressions or recesses, or a combination thereof.

At least some of the microstructured features can be formed on a nano-, micro- or macro-scale. Each microstructured feature can be defined by two or more dimensions (e.g., one or more dimensions into/out of the plane of the first major surface 108 and one or more dimensions in the plane of the first major surface 108). In some embodiments, the first major surface 108 includes a configuration of microstructured features, such that at least two dimensions of each of the features are microscopic. The "features" can include any of the above-described microstructured features formed in the first major surface 108 of the substrate 102, including the walls 112, the wells 114, the protrusions 126, or any other microstructured features formed on the first major surface 108. "Microscopic features" are sufficiently small so as to require an optic aid to the naked eye to determine their shape. In some embodiments, the dimensions of the microstructured features can be no greater than 200 micrometers in at least two of the possible dimensions.

The microstructured features can have a desired characteristic size (e.g., length, width, depth, radius, diameter, or other dimension measured along any direction) and density (e.g., features per unit area of the first major surface 108). A feature can be configured such that its characteristic length in all three directions (e.g., x, y (in the plane of the first major surface 108) and z (into/out of the plane of the first major surface 108)) is similar. Alternatively, a feature can be configured such that the characteristic length in one or more directions is greater than in the other directions.

In some embodiments, a feature can have a maximum characteristic length in one or more dimensions of no greater than about 500 micrometers. In some embodiments, the maximum characteristic length is 50 micrometers, and in some embodiments, the characteristic maximum length is 10 micrometers. In some embodiments, the minimum characteristic length in one or more dimensions is 1 nanometer. In some embodiments, the minimum characteristic length is 10 nanometers, and in some embodiments, the minimum characteristic length is 100 nanometers. Furthermore, in some embodiments, the feature density is at least 100 features per square millimeter ($mm^2$), in some embodiments, at least 1,000 features per $mm^2$, and in some embodiments, at least 10,000 features per $mm^2$.

As discussed above, the adhesive 119 allows the microstructured antimicrobial film 100 to be coupled to a variety of surfaces. In some embodiments, as described below, the adhesive 119 provides good adhesion to a surface, while also being removable under moderate force without leaving a residue (e.g., removable and/or repositionable pressure sensitive adhesives). Examples of suitable materials for the adhesive 119 include one or more adhesives based on (meth) acrylates, urethanes, silicones, epoxies, rubber based adhesives (including natural rubber, polyisoprene, polyisobutylene, and butyl rubber, block copolymers, and thermoplastic rubbers), and combinations thereof.

Examples of suitable (meth)acrylates include polymers of alkyl acrylate monomers such as methyl methacrylate, ethyl methacrylate, n-butyl methacrylate, methyl acrylate, ethyl acrylate, n-butyl acrylate, iso-octyl acrylate, iso-nonyl acrylate, 2-ethyl-hexyl acrylate, decyl acrylate, dodecyl acrylate, n-butyl acrylate, hexyl acrylate, and combinations thereof.

Examples of commercially available block copolymers include those available under the trade designation "KRATON G-1657" from Kraton Polymers, Westhollow, Tex.

As described above, in some embodiments, the adhesive 119 can include a removable and/or repositionable pressure sensitive adhesive. An adhesive is considered to be "removable," if after final application to an intended substrate, the microstructured antimicrobial film 100 can be removed at the end of the intended life of the article at a rate in excess of 7.62 meters/hour (25 feet/hour) by hand with the optional use of heat without damage to either the microstructured antimicrobial film 100 or the surface to which it is coupled. In some embodiments, the removable pressure sensitive adhesive has a 180 degree peel strength (from a sheet of 400-gauge Mylar D PET film, available from the E.I. du Pont de Nemours and Company, Wilmington, Del.) of less than 8 N/cm, and more particularly, less than 6 N/cm.

The term "repositionable" generally refers to the ability to be, at least initially, repeatedly adhered to and removed from a surface without substantial loss of adhesion capability. In some embodiments, the repositionable pressure sensitive adhesive has a 180 degree peel strength, at least initially, of less than about 2 N/cm, in some embodiments, less than about 1 N/cm, and in some embodiments, less than about 0.1 N/cm, when peeled from a sheet of 400-gauge Mylar D PET film, available from the E.I. du Pont de Nemours and Company, Wilmington, Del.

Examples of suitable removable and repositionable pressure sensitive adhesives include those described in Hobbs et al., U.S. Publication No. 2005/0249791 and Cooprider et al., U.S. Pat. No. 5,571,617; and adhesives based on solid inherently tacky, elastomeric microspheres, such as those disclosed in Silver, U.S. Pat. No. 3,691,140, Merrill et al., U.S. Pat. No. 3,857,731, and Baker et al., U.S. Pat. No. 4,166,152.

In some embodiments, the adhesive 119 includes an electrostatic charge. In some embodiments, the adhesive 119 itself is an electrostatic charge that can be imparted to the microstructured antimicrobial film 100 (i.e., the second side 106 of the substrate 102). Alternatively, in some embodiments, the adhesive 119 combines an electrostatic charge with other adhesive components. In embodiments employing an electrostatic adhesive 119, the adhesive 119 can have a permanent electrostatic charge and can exhibit electrostatic attraction to a wide variety of surfaces thereby allowing the film to be removably (and/or repositionably) coupled to desired surface(s). Permanent electrostatic charge can be imparted to the microstructured antimicrobial film 100 (e.g., to the substrate 102, or to the adhesive 119) using corona charging (e.g., nitrogen or air), as described in Everaerts et al., U.S. Publication No. 2005/0000642.

In some embodiments, the adhesive 119 can include an additional antimicrobial material to provide an additional source of antimicrobial activity. This can extend the useful life of the microstructured antimicrobial film 100, as described in Hobbs et al., U.S. Publication No. 2005/0249791. Examples of suitable antimicrobial materials include those discussed below for the antimicrobial material 120.

In some embodiments, the adhesive 119 exhibits sufficient optical quality and light stability such that the adhesive 119 does not yellow with time or upon weather exposure so as to degrade the viewing quality of an underlying surface. The adhesive 119 may be applied using a variety of known coating techniques such as transfer coating, knife coating, spin coating, die coating and the like. Additional examples of suitable adhesives include those described in Draheim et al., U.S. Publication No. 2003/0012936. Several of such adhesives are commercially available under the trade designations "8141", "8142", and "8161" adhesives from 3M Company, St. Paul, Minn.

In some embodiments, as shown in FIGS. 1 and 2, the adhesive 119 can be substantially smooth. In some embodiments, the adhesive 119 can be textured or include a topography. A topography can be beneficial for bleeding air out from beneath the microstructured antimicrobial film 100 as it is applied to a surface, thereby reducing the amount of trapped air pockets beneath microstructured antimicrobial film 100. Examples of suitable topographies are discussed in Sher et al., U.S. Pat. No. 6,911,243.

In some embodiments, the thickness of the adhesive 119 (if employed) can be at least about 10 micrometers, in some embodiments, at least about 20 micrometers, and in some embodiments, at least about 50 micrometers. In some embodiments, the thickness of the adhesive 119 can be no greater than about 300 micrometers, in some embodiments, no greater than about 200 micrometers, and in some embodiments, no greater than about 100 micrometers.

The antimicrobial material 120 is illustrated in FIGS. 1 and 2 by of example only as being a liquid; however, it should be understood that the antimicrobial material 120 can include a solid, a liquid, a semi-solid, a gelatinous material, or a combination thereof. The antimicrobial material 120 can be at least partially flowable (e.g., a flowable liquid including highly viscous liquids, or a flowable solid such as a powder) to facilitate positioning the antimicrobial material 120 in the wells 114 of the microstructured antimicrobial film 100. Furthermore, the antimicrobial material 120 does not need to be in the form of a continuous layer, but rather can be discrete, continuous, or a combination thereof. The antimicrobial material 120 can include one or more antimicrobial agents that are adapted to provide one or more forms of antimicrobial activity. In some embodiments, the antimicrobial material 120 includes the antimicrobial agent(s) alone, and in some embodiments, the antimicrobial material 120 includes other materials, such as a solvent (or a dispersant, a surfactant, an emulsifier, etc.), a polymer binder, and the like, or combinations thereof.

The antimicrobial agent can be provided in the antimicrobial material 120 in a variety of forms, including, but not limited to, (1) an antimicrobial agent dispersed in a liquid solvent, (2) a liquid antimicrobial agent, (3) a solid antimicrobial agent (e.g., powdered or dried to form a coating or layer of the antimicrobial material 120), (4) an antimicrobial agent dispersed or dissolved in a polymer binder, or a combination thereof. An example of a combination can include an antimicrobial agent dispersed within the interstices of a hydrogel (e.g., the antimicrobial agent can be dissolved in water contained in the polymer matrix of the hydrogel, such that the antimicrobial material 120 includes a solvent and a polymer). In embodiments employing an antimicrobial agent dispersed in a liquid solvent or a polymer, the antimicrobial material 120 positioned in the wells 114 of the microstructured antimicrobial film 100 can be dried to remove at least a portion of a solvent to form a solid, semi-solid or gelatinous antimicrobial material 120.

The antimicrobial material 120 can include a variety of antimicrobial agents, including a variety of organic antimicrobial agents (e.g., including small molecules, polymers, or combinations thereof), a variety of inorganic antimicrobial agents, or a combination thereof. The antimicrobial material 120 can include one or more antimicrobial agents. Examples of suitable inorganic antimicrobial agents can include, but are not limited to, transition metal ion-based compounds, (e.g., silver, zinc, copper, gold, tin and platinum-based compounds), iodophors, and combinations thereof.

Examples of suitable silver-containing antimicrobial agents include silver sulfate, silver acetate, silver chloride, silver lactate, silver phosphate, silver stearate, silver thiocyanate, silver proteinate, silver carbonate, silver nitrate, silver sulfadiazine, silver alginate, silver nanoparticles, silver-substituted ceramic zeolites, silver complexed with calcium phosphates, silver-copper complexed with calcium phosphates, silver dihydrogen citrates, silver iodines, silver oxides, silver zirconium phosphates, silver-substituted glass, aqueous solutions of silver salts and/or oxides complexed with various ammonium salts, and combinations thereof.

Suitable commercially available silver-containing antimicrobial agents can include silver zeolites, such as those sold under the trade designation "AGION" from AgION Technologies Inc., Wakefield, Mass.; AgZn zeolites, available under the trade designations "IRGAGUARD B5000" and "IRGAGUARD B8000" from Ciba Specialty Chemicals, Tarrytown, N.Y.; silver sodium hydrogen zirconium phosphates, available under the trade designation "ALPHASAN" from Milliken Chemicals, Spartanburg, S.C.; silver nanoparticles, available from Nucryst Pharmaceuticals, Wakefield, Mass. and from Advanced Nano Products Co., Ltd., Korea; silver or copper silver complexed with calcium phosphates, available from Giltech, Ltd., Scotland; other possible silver containing antimicrobical additives, available from Aegis Environments, Midland, Mich.; silver dihydrogen citrate, available from Pure Biosciences, El Cajon, Calif.; silver iodine, available from Surfacine Development Co., Tyngsborough, Mass.; silver substituted glasses available under the trade designation "IONPURE" from Ishizuka Glass, Ishizuka Glass Co., Ltd., Japan; and combinations thereof.

Iodine and its various complexed forms are commonly referred to as iodophors. Iodophors can include complexes of elemental iodine or other iodine species (e.g., triodide) with certain carriers or binder. Iodophors can be formed between elemental iodine or other iodine species, and a polymer binder (e.g., polyethylene glycol) in the antimicrobial material 120. Such iodophors can function by not only increasing the iodine solubility but by reducing the level of free molecular iodine in solution and by providing a type of sustained release reservoir of iodine. Iodophors can be formed using polymeric binders such as polyvinylpyrrolidone (PVP); copolymers of N-vinyl lactams with other unsaturated monomers such as, but not limited to, acrylates and acrylamides; various polyether glycols (PEGs) including polyether-containing surfactants such as nonylphenolethoxylates and the like; polyvinyl alcohols; polycarboxylic acids such as polyacrylic acid; polyacrylamides; and polysaccharides such as dextrose. Other suitable iodophors include the protonated amine oxide surfactant-triiodide complexes described in U.S. Pat. No. 4,597,975 (Woodward et al.). In some applications, the iodophor is povidone-iodine. This can be obtained commercially as povidone-iodine USP, which is a complex of K30 polyvinylpyrrolidone and iodide wherein the available iodine is present at about 9 weight percent to about 12 weight percent.

Examples of suitable organic antimicrobial agents can include, but are not limited to, quaternary ammonium compounds, such as polymeric quaternary ammonium salts such as 2-butenyldimethyl ammonium chloride polymers commercially available under the trade designation "POLYQUAT" from Arch Chemicals, Inc., Norwalk, Conn., and available under the trade designation "BARDAC", from Lonza Group Ltd., Valais, Switzerland; phenolic compounds such as phenol and its derivatives, parabens (e.g., methyl parabens, ethyl parabens, propyl parabens, butyl parabens), and triclosan, which has the chemical formula 2,4,4'-trichloro-2'-hydroxy diphenyl ether, and is commercially available from Ciba Specialty Chemicals, Tarrytown, N.Y. and Microban International, Ltd., Huntersville, N.C.; parachlorometaxylenols (PCMX); poly(iminoimidocarbonyl-imidocarbonyliminohexamethylene hydrochlorides), commercially available under the trade designation "VANTOCIL P" from Arch Chemicals, Inc., Norwalk, Conn.; octenidenes; 2-bromo-2-nitropropane-1,3 diol; hexachlorophenes; biguanide compounds (e.g., halogenated hexidines such as chlorhexidine, chlorhexidine gluconate (CHG), and chlorhexidine acetate); polyhexamethylene biguanides; antimicrobial lipids such as those disclosed in Scholz et al., U.S. Publication No. 2005/0089539; antimicrobial acids (e.g., fatty acids, benzoic acids, and salicylic acids); antimicrobial natural oils (e.g., tea tree oils, and grape fruit seed extracts); organic salts of transition metals (i.e., organometallic antimicrobial agents), such as silver salts (e.g., silver lactate), copper salts (e.g., copper napthenate), zinc salts, and tin salts (e.g., trialkyl tin hydroxides and triaryl tin hydroxides); halogen-containing compounds (e.g., hypochlorite (e.g., bleach)) and combinations thereof.

Suitable antimicrobial lipids can include, for example, fatty acid monoesters/monoethers. The term "fatty acid monoesters/monoethers" generally refers to fatty acid monoesters, fatty acid monoethers, or a combination thereof. In some embodiments, the fatty acid monoesters/monoethers suitable for the antimicrobial agent are considered food grade and Generally Recognized As Safe (GRAS) by the U.S. Food and Drug Administration (FDA). Such fatty acid monoesters/monoethers may be derived from C8 to C12 fatty acids such as glycerol monoesters of caprylic acid, capric acid, and lauric acid; propylene glycol monoesters of caprylic acid, capric acid, and lauric acid; and combinations thereof. Examples of suitable fatty acid monoesters include, but are not limited to, glycerol monolaurate, commercially available under the trade designation "LAURICIDIN" from MedChem Laboratories, East Lansing, Mich.; glycerol monocaprylate, commercially available under the trade designation "POEM M-100" from Riken Vitamin Ltd., Tokyo, Japan; glycerol monocaprate, commercially available under the trade designation "POEM M-200" from Riken Vitamin Ltd.; propylene glycol monolaurate, propylene glycol monocaprylate, and propylene glycol monocaprate, all commercially available from Uniquema International, Chicago, Ill.; and combinations thereof.

Examples of suitable concentrations of the fatty acid monoesters/monoethers range from about 1.0% to about 30.0% by weight. Examples of particularly suitable concentrations of the fatty acid monoesters/monoethers in the composition range from about 5.0% to about 20.0% by weight.

The antimicrobial material 120 may also include an enhancer and/or a surfactant for use with the fatty acid monoesters/monethers, as discussed in Andrew et al., PCT application No. WO 00/71183, entitled "Antimicrobial Articles," and in Andrews et al., PCT Application No. WO01/43549, entitled "Fruit, Vegetable, and Seed Disinfectants." The enhancers and/or surfactant can be provided as a solution comprising the dissolved enhancer and/or surfactant in an aqueous or non-aqueous solvent. Examples of such solvents can include water, isopropyl alcohol, or combinations thereof.

In some embodiments, the antimicrobial performance of the antimicrobial material 120 can be increased by incorporating two or more antimicrobial agents (e.g., two or more antimicrobial agents that produce a synergistic effect). An example of a suitable synergistic composition can include a quaternary amine salt such as 2-butenyldimethyl ammonium chloride polymers commercially available under the trade designation "POLYQUAT" from Arch Chemicals, Inc., Norwalk, Conn., and an inorganic silver compound. For example, the quaternary amine salt can provide faster antimicrobial activity against gram (+) bacteria, while silver compounds can provide a slower but broader antimicrobial activity against both gram (+) and gram (−) bacteria, viruses, and fungi.

Suitable concentrations of the antimicrobial agent in antimicrobial material 120 can include concentrations that are high enough to produce antimicrobial activity, and low enough such that the antimicrobial agent does not phase separate from other materials (if present) in the antimicrobial material 120. Examples of suitable antimicrobial agent concentrations in the antimicrobial material 120 generally range from about 1% by weight to about 50% by weight. However, the suitable concentrations may vary depending on the antimicrobial agent used, the type of antimicrobial material 120 used (e.g., dispersed in a solvent, dispersed in a polymer binder, etc.), and the desired level of antimicrobial activity.

Suitable concentration ranges for inorganic antimicrobial agents in the antimicrobial material 120 can range from about 1% by weight to about 20% by weight, while particularly suitable concentrations can range from about 5% by weight to about 10% by weight. Such concentrations can provide suitable antimicrobial activity without negatively impacting the properties of the antimicrobial material 120.

As mentioned above, the antimicrobial material 120 can, in some embodiments, include one or more antimicrobial agents that are dispersed or dissolved within a polymer binder. The polymer can function to bind and hold the antimicrobial agent within the wells 114. Suitable polymers for use in the antimicrobial material 120 can include, but are not limited to, water-soluble polymers, organic solvent-soluble polymers, water-based polymer dispersions, radiation curable polymers, and combinations thereof.

Examples of water-soluble polymers can include polyvinyl alcohols, polyvinylpyrrolidones, polyethylene oxides, sulfonated polyurethanes, copolymers thereof, and combinations thereof. Commercially available polyvinyl alcohols can include those sold under the trade designation POLYVINYL ALCOHOL from J. T. Baker (Phillipsburg, N.J.) and from Sigma-Aldrich Chemical Company (Saint, Louis, Mo.). Commercially available polyvinylpyrrolidones can include those available from J. T. Baker and the like of PVP-Kxx available from Peakchem (ZheJiang, China), for example PVP-K90 and PVP-K30, where the number after the letter K indicates the average molecular weight of the polymer. Commercially available polyethylene oxide polymers can include those sold under the trade designation "Polyox" available from Dow Chemical Co., Midland, Mich.

Organic solvent-soluble polymers can include polyurethanes, acrylic polymers, polyamides, copolymers thereof, and combinations thereof. Commercially available solvent-based polyurethanes can include those available under the trade designation PERMUTHANE from Stahl USA, Peabody, Mass., such as SU26-248, an aliphatic polyurethane in toluene. Other suitable polyurethanes can include Estanes available from B.F. Goodrich (Cleveland, Ohio), such as Estane 5715 and 5778, and Morthanes available from Huntsman polyurethanes (Ringwood, Il), such as CA118 and CA237, both of which are polyester polyurethanes. Other suitable polymers can include those available from NeoResins DSM under the trade designation U-371.

Examples of water-based polymer dispersions can include polyurethanes, polyureas, polyacrylics, polyethers, polyester, and copolymers thereof and combinations thereof. Suitable aqueous dispersions can include urethanes such as those available under the trade designation NEOREZ from DSM NeoResins, Wilmington, Mass., particularly NEOREZ R-960 and NEOREZ R-9699; acrylics such as those available under the trade designation NEOCRYL from DSM NeoResins, such as NEOCRYL XK-90, NEOCRLYL XK-96 and NEOCRYL XK-95; and, acrylic urethane copolymers, such as those available under the trade designation NEOPAC from DSM NeoResins. Other water-based urethanes can include RU-077 and RU-075 available from Stahl USA, Peabody, Mass.

The above-listed polymers may also be partially or fully cross-linked to reduce the water solubility of such materials. Polymers having reduced water solubility can be beneficial for use on surfaces that come into contact with water (e.g., surfaces that are rinsed or soaked with water). To initiate the cross-linking, the antimicrobial material 120 (or the polymeric portion thereof) can include cross-linking agents, such as chain extension agents and chemical cross-linking agents. Examples of cross-linking agents can include isocyanates such as those available under the trade designation DESMO-DUR from Bayer AG (Pittsburg, Pa.), aziridine crosslinkers such as those available under the trade designation CX-100 from DSM NeoResins and those available under the trade designation XR-2500 from Stahl USA. Suitable chain extension agents can include carbodiimides, such as those available under the trade designation EX62-944, and melamines such as those available under the trade designation XR-9174, both available from Stahl USA.

Examples of suitable cross-linkable polymer compositions include self cross-linking polymer dispersions, where the deposited coating self cross-links upon drying to form a durable coating layer. Self cross-linking polymer dispersions typically contain side groups that react to form chemical bonds via condensation polymerizations, which take place upon evaporation of water. Self cross-linking polymer dispersions offer the advantage of forming an antimicrobial material 120 that is solvent resistant without requiring cross-linking agents.

Examples of self cross-linking urethane dispersions can include polyester-urethanes that are terminated by hydrolysable silyl groups and contain solubilizing sulfonic acid functional groups. Such polyester-urethanes are described in Krepski, et al., U.S. Pat. No. 5,929,160. Additional examples of suitable self cross-linking urethane dispersions can include polyurethane water-based dispersions containing hydroxyl groups to accomplish the self cross-linking function. Suitable hydroxyl group-based polyurethanes can include those prepared pursuant to the process described in Mazanek et al., U.S. Patent Publication No. 2003/0199632. Even further additional examples of suitable self cross-linking urethane dispersions can include polyurethane polymer hybrid dispersions based on oxidatively drying polyols, such as those disclosed in Ingrisch et al., U.S. Pat. No. 6,462,127.

Examples of commercially available self cross-linking polymers include dispersions sold under the trade designations "RHEOPLEX" and "ROVACE," available from Rohm and Haas Company, Philadelphia, Pa., which are typically used as binders for textile and non-woven substrates for the protection of color dyes applied to the substrates. Exemplary compositions include the trade designated "RHEOPLEX HA-12" (non-ionic dispersion with glass transition temperature of about 19° C.) and "RHEOPLEX TR-407" (anionic dispersion with glass transition temperature of 34° C.), both of which exhibit good wash durability and chemical resistance. Additional examples of commercially available self cross-linking polymers can include the trade designated "NEOREZ R-551" polyether-based polymers and "NEOCRYL XK-98" acrylic emulsion polymers, both of which are available from DSM NeoResins, Wilmington, Mass.

Examples of radiation curable polymers can include those described in Ylitalo et al., PCT Publication No. WO 2007/070650.

While shown as a single layer of material in FIGS. 1 and 2, the antimicrobial material 120 can alternatively include multiple antimicrobial materials, or multiple antimicrobial material layers (e.g., polymerized layers). In such embodiments, the antimicrobial material 120 can include concentration gradients of antimicrobial agents. For example, the concentration of antimicrobial agent(s) can be inversely proportional to the distance from the base 116 of a well 114 in which the antimicrobial material 120 is positioned, such that the highest concentration of antimicrobial agent(s) is adjacent the base 116 of a given well 114.

In some embodiments, the antimicrobial material 120 can include other additives or adjuvants, including, but not limited to, matting agents, colorants (e.g., pigments and/or dyes), rheology modifiers, wetting agents, stabilizers (e.g., ultraviolet (UV) light stabilizers, free-radical scavengers, etc.), surfactants, fragrances, or a combination thereof.

Examples of suitable commercially available UV light stabilizers can include, but are not limited to, benzophenone-type UV absorbers, which are available under the trade designation "UVINOL 400" from BASF Corp., Parsippany, N.J.; under the trade designation "CYASORB UV-1164" from Cytec Industries, West Patterson, N.J.; and under the trade designations "TINUVIN 900", "TINUVIN 123" and "TINUVIN 1130" from Ciba Specialty Chemicals, Tarrytown, N.Y. Examples of suitable concentrations of ultraviolet light stabilizers in the antimicrobial material 120 range from about 0.1% by weight to about 10% by weight, with particularly suitable total concentrations ranging from about 1% by weight to about 5% by weight.

Examples of suitable free-radical scavengers can include, but are not limited to, hindered amine light stabilizer (HALS) compounds, hydroxylamines, sterically hindered phenols, and combinations thereof. Examples of suitable commercially available HALS compounds include the trade designated "TINUVIN 292" from Ciba Specialty Chemicals, Tarrytown, N.Y., and the trade designated "CYASORB UV-24" from Cytec Industries, West Patterson, N.J. Examples of suitable concentrations of free-radical scavengers in the antimicrobial material 120 range from about 0.05% by weight to about 0.25% by weight.

Examples of suitable surfactants can include, but are not limited to, anionic, cationic, non-ionic, and zwitterionic surfactants and emulsifiers, such as those disclosed in Scholz et al., U.S. Pat. No. 5,951,993, and combinations thereof. Additional examples of suitable surfactants can include, but are not limited to, polyalkoxylated block copolymer surfactants, silicone copolyols, polyethylene oxide alkyl and/or aryl ethers and esters, and combinations thereof.

The liquid antimicrobial material 120 illustrated in FIGS. 1 and 2 is further illustrated by way of example only as being a liquid having a concave meniscus (i.e., a liquid having molecules that attract those of the substrate 102, or a coating formed thereon). This is shown by way of example only for the purpose of illustration, but it should be understood that the antimicrobial material 120 could instead be a liquid having a convex meniscus (i.e., a liquid having molecules that repel those of the substrate 102, or a coating formed thereon) or little to no meniscus. In the embodiment illustrated in FIGS. 1 and 2, the upper surface 122 of the antimicrobial material 120 is any portion of top surface of the liquid antimicrobial material 120. In embodiments employing other forms of the antimicrobial material 120, the upper surface 122 is the top surface of the antimicrobial material 120 at any position within the well 114. For example, in embodiments employing a powdered antimicrobial material 120, the upper surface 122 is the top of the powder positioned in the well 114. In some embodiments, the powder can be attracted to an inner surface of the well 114 by an interaction, such as an electrostatic interaction, which can facilitate the retention of the powdered antimicrobial material 120 within the well 114.

As mentioned above, the microstructured antimicrobial film 100 can be used in a variety of applications, including as a wrap material (e.g., food wrap), as a surface protection film for a variety of environmental surfaces, and combinations thereof. In embodiments employing the adhesive 119, the adhesive 119 can facilitate coupling the microstructured antimicrobial film 100 to a surface. The terms "surface" or "environmental surface" generally refer to any surface to which the microstructured antimicrobial film 100 can be coupled. The surface can be present in a variety of locations, including, but not limited to, healthcare facilities (e.g., hospitals, doctor offices, etc.), daycare facilities, schools, swimming pools, restrooms (e.g., commodes, sinks, shower stalls), locker rooms, fitness facilities (e.g., group fitness studios, gyms, etc.), long term care facilities (e.g., nursing homes), food processing plants, homes, offices, food service facilities, hotels, transportation vehicles (e.g., automobiles, buses, trains, airplanes, boats, cruise ships, etc.), etc. Examples of surfaces can include, but are not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, food preparation surfaces, equipment surfaces, clothing, etc., and combinations thereof.

In any of the above-described uses of the microstructured antimicrobial film 100, the microstructured surface 108 of the microstructured antimicrobial film 100, and particularly, the wells 114, provide storage areas or reservoirs for the antimicrobial material 120, which can provide long-term, controlled release of the antimicrobial agent to combat microbes that come into contact with (or near) the first side 104 of the microstructured antimicrobial film 100. In addition, in embodiments employing the adhesive 119, the microstructured configuration of the microstructured antimicrobial film 100 can eliminate the need for a release liner or a low adhesion backside (LAB) coating on the second side 106 of the microstructured antimicrobial film 100. As a result, the microstructured antimicrobial film 100 can be rolled upon itself to form a roll, or a plurality of microstructured antimicrobial films 100 can be stacked on top of one another, without requiring a release liner.

Furthermore, the microstructured configuration of the microstructured antimicrobial film 100 facilitates the retention of the antimicrobial material 120 in the wells 114 to avoid transferring the antimicrobial material 120 to objects, food, people and/or surfaces that may come into contact with the first side 104 of the microstructured antimicrobial film 100. For example, the microstructured antimicrobial film 100 can be used as a food wrap or food packaging material (e.g., "active food packaging"). Some food grade antimicrobial compositions can flake or peel off when coated onto a smooth film, and which can alter the appearance and/or flavor of food that comes into contact with the film. In addition, some antimicrobial compositions can leave a greasy or sticky residue when coated onto a smooth substrate. However, the microstructured surface 108 of the microstructured antimicrobial film 100, and particularly, the wells 114, are adapted to retain the antimicrobial material 120 to inhibit the antimicrobial material 120 from being transferred from the microstructured antimicrobial film 100 during normal usage or from providing an undesirable residue, while still providing antimicrobial activity.

Images (e.g., decorative patterns, logos and/or alphanumeric characters) can be applied either to the second side 106 of the microstructured antimicrobial film 100, or to the exposed side of the adhesive 119 (if employed). In embodiments employing an imaged second side 106 of the substrate 102 and an adhesive 119, the adhesive 119 can be transparent. An image can be applied using a variety of techniques, including any of the printing or coating methods described above.

Depending on the printing method and the ink used, it may be necessary to apply an ink receptive coating to the second side 106 of the substrate 102 to facilitate printing an image. When the microstructured antimicrobial film is intended to be used in food contact applications, the ink receptive coating can comprise a food grade, Generally Recognized As Safe (GRAS) and/or FDA-approved coating, and the ink (or coating) can comprise a food grade, GRAS and/or FDA-approved ink.

In some embodiments, the microstructured antimicrobial film 100 can include an end-of-service indicator to provide visual indication prompting the user to replace the microstructured antimicrobial film 100. Examples of suitable end-of-service indicators include time-temperature indicators and color changing dyes. An end-of-service indicator can be applied, for example, to the microstructured antimicrobial film 100 in the form of a label or paint to the corners of the first side 104 of the microstructured antimicrobial film 100 after the microstructured antimicrobial film 100 has been coupled to a surface. In some embodiments, the indicator is calibrated to indicate a color change at about the time when the corresponding microstructured antimicrobial film 100 should be replaced (e.g., when the antimicrobial activity levels have substantially decreased or are exhausted).

Time-temperature indicators typically operate by chemical reaction mechanisms, diffusion mechanisms, and capillary driven, fluid-wicking mechanisms. Examples of suitable time-temperature indicators are disclosed in Bommarito, et al., U.S. Pat. No. 6,741,523 (i.e., microstructured time-dependent indicators) and Arens, et al., U.S. Pat. No. 5,667,303, and in The Wiley Encyclopedia of Packaging Technology, 400-406 (John Wiley & Sons, 1986) under the section entitled "Indicating Devices". Examples of suitable commercially available time-temperature indicators include those sold under the trade designations "MONITOR MARK" from 3M Company, St. Paul, Minn.; "WARM MARK" from Dry Pak Industries, Studio City, Calif.; "FRESH CHECK" from Lifelines Technology Inc., Morris Plains, N.J.; "VISTAB" from Visual Indicator Tag Systems AB, Malmö, Sweden; and "TT MONITOR" from Avery Dennison Corporation, Pasadena, Calif.

The microstructured antimicrobial film 100 can be provided to an end user in a variety of arrangements. For example, microstructured antimicrobial film 100 can be provided as a single sheet (e.g., to be used as a wrap material or as an adhesive sheet to be coupled to surface), or as a roll of tear-away film that allows consumers to remove desired amounts of the microstructured antimicrobial film 100 for individualized uses. Alternatively, the microstructured antimicrobial film 100 can be provided with pre-cut dimensions to fit industry standard components, such as touch-screen displays. The microstructured antimicrobial film 100 can also be tailored to specific uses by varying the types and concentrations of the antimicrobial agents in the antimicrobial material 120. For example, the microstructured antimicrobial film 100 can include antimicrobial agents that are effective against particular pathogens (e.g., gram positive or gram negative pathogens) or combinations of pathogens.

Antimicrobial activity can be quantified in a variety of ways. Two exemplary quantification assays described and exemplified herein are the Zone of Inhibition Assay and Microbial Load Reduction Assay. The "zone of inhibition" refers to the zone of inhibition obtained pursuant to the Zone of Inhibition Assay Method described in the Examples section below. The "microbial load reductions" refer to microbial load reductions obtained pursuant to the Microbial Load Reduction Assay described in the Examples section below.

Examples of suitable levels of antimicrobial activity include zones of inhibition of at least about 1 mm outside the edge of the microstructured antimicrobial film for at least one of *Staphylococcus aureus* (gram positive) and *Pseudomonas aeruginosa* (gram negative) pathogens. By way of example only, disk-shaped microstructured antimicrobial films are used in the Zone of Inhibition Assays in the Examples below, but it should be understood that the Zone of Inhibition Assay is not dependent on film size or shape. As such, the zones of inhibition are defined here as the distance beyond the microstructured antimicrobial film where growth remains inhibited. For example, a zone of inhibition of at least about 1 mm outside the edge of the microstructured antimicrobial film signifies that the microstructured antimicrobial film successfully inhibited growth of at least one of *S. aureus* (gram positive) and *P. aeruginosa* (gram negative) pathogens in the area under the microstructured antimicrobial film, as well as the area extending 1 mm in all directions outside the edge of the film.

Further examples of suitable levels of antimicrobial activity include zones of inhibition of at least about 3 mm outside the edge of the film for at least one of *S. aureus* (gram positive) and *P. aeruginosa* (gram negative) pathogens. Examples of particularly suitable levels of antimicrobial activity include zones of inhibition of at least about 1 mm outside the edge of the film for both of *S. aureus* (gram positive) and *P. aeruginosa* (gram negative) pathogens. Examples of even more particularly suitable levels of antimicrobial activity include zones of inhibition of at least about 3 mm outside the edge of the film for both of *S. aureus* (gram positive) and *P. aeruginosa* (gram negative) pathogens.

Additional examples of suitable levels of antimicrobial activity, and particularly, biocidal activity, include microbial load reductions of at least about 90% for at least one of *S. aureus* (gram positive) and *P. aeruginosa* (gram negative) pathogens. Further examples of suitable levels of antimicrobial activity include microbial load reductions of at least about 99% for at least one of *S. aureus* (gram positive) and *P. aeruginosa* (gram negative) pathogens. Examples of particularly suitable levels of antimicrobial activity include microbial load reductions of at least about 90% for both of *S. aureus* (gram positive) and *P. aeruginosa* (gram negative) pathogens. Finally, examples of even more particularly suitable levels of antimicrobial activity include microbial load reductions of at least about 99% for both of *S. aureus* (gram positive) and *P. aeruginosa* (gram negative) pathogens.

When removing and/or replacing the microstructured antimicrobial film 100 from a surface, a user may peel the microstructured antimicrobial film 100 with a moderate force to delaminate the adhesive 119 (or disrupt the electrostatic interaction) from the surface. The user can then dispose of the used microstructured antimicrobial film 100, and can adhere a second microstructured antimicrobial film 100 to the surface to further extend the period of protection against pathogen contamination. Alternatively, the microstructured antimicrobial film 100 can be one of a plurality of microstructured antimicrobial films 100 provided in a stack, which will be described in greater detail below with reference to FIG. 3. The stack can then be adhered to the surface, and the uppermost microstructured antimicrobial film 100 in the stack can be peeled from the stack to expose a fresh microstructured antimicrobial film 100.

Figure 3:
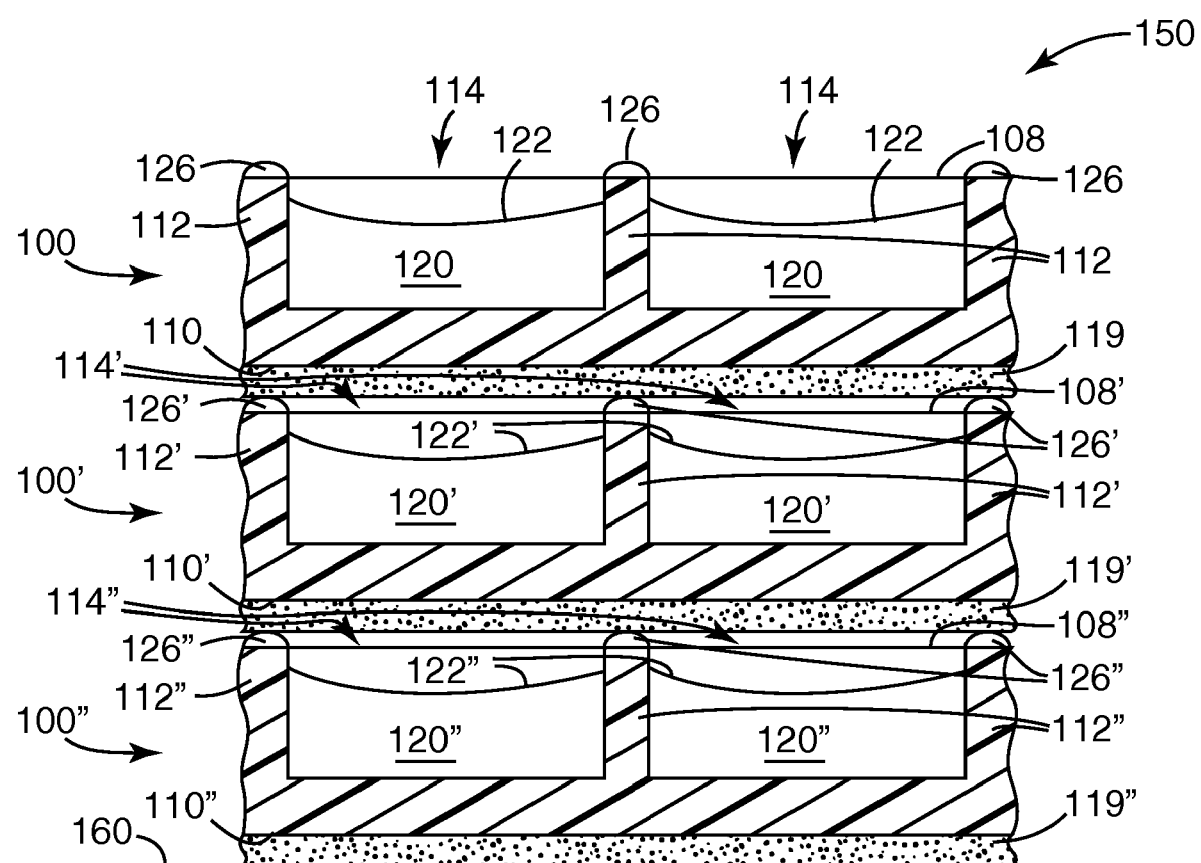
FIG. 3 is a schematic cross-sectional side view of an antimicrobial film assembly according to one embodiment of the present disclosure, the antimicrobial film assembly comprising the microstructured antimicrobial film of FIGS. 1 and 2.

FIG. 3 illustrates an antimicrobial film assembly or a multilayer antimicrobial film 150, according to one embodiment of the present disclosure, coupled to a surface 160. The antimicrobial film assembly 150 includes three microstructured antimicrobial films by way of example only, particularly, a first microstructured antimicrobial film 100, a second microstructured antimicrobial film 100', and a third microstructured antimicrobial film 100". Each of the microstructured antimicrobial films 100, 100', 100" includes all of the features and elements (and alternatives to such features and elements) as the microstructured antimicrobial film 100 described above with respect to FIGS. 1 and 2. For simplicity, when the description applies equally to all of the microstructured antimicrobial films 100, reference numerals without primes will be used, but it should be understood that such a description applies equally to each of the microstructured antimicrobial films 100 of the antimicrobial film assembly 150.

FIG. 3 illustrates that a plurality of microstructured antimicrobial films 100 can be positioned on top of one another in the form of a stack. Alternatively, however, FIG. 3 (if shown without the surface 160) can also be used to illustrate a section of a roll that is formed by rolling one microstructured antimicrobial film 100 upon itself. For the purpose of illustration only, the antimicrobial film assembly 150 includes three microstructured antimicrobial films 100, 100' and 100" in the form of a stack. It should be understood, however, that the antimicrobial film assembly 150 can include as many or as few microstructured antimicrobial films 100 as necessary for a particular application.

The antimicrobial film assembly 150 can be coupled to the surface 160 that is desired to have antimicrobial activity. As shown in FIG. 3, the first microstructured antimicrobial film 100 forms the top layer in the antimicrobial film assembly 150, and the third microstructured antimicrobial film 100" forms the bottom layer in the antimicrobial film assembly 150. As a result, the third adhesive 119", which is coupled to the second major surface 110" of the third microstructured antimicrobial film 100", is coupled to the surface 160; the second adhesive 119', which is coupled to the second major surface 110' of the second microstructured antimicrobial film 100', is further coupled to the first major surface 108" of the third microstructured antimicrobial film 100"; and the first adhesive 119, which is coupled to the second major surface 110 of the first microstructured antimicrobial film 100, is further coupled to the first major surface 108' of the second microstructured antimicrobial film 100'. Particularly, the first and second adhesives 119, 119' are shown as being coupled to the protrusions 126', 126" of the second and third first major surfaces 108', 108".

In some embodiments, such as that of FIG. 3, the adhesives 119 are selected to demonstrate limited cold flow. For example, in some embodiments, the adhesive 119 of the first microstructured antimicrobial film 100 has limited cold flow to limit the ability of the adhesive 119 to flow into the wells 114' of the second microstructured antimicrobial film 100', where it may come into contact with (and may disrupt) the antimicrobial material 120'.

By providing the first major surfaces 108 of the microstructured antimicrobial films 100 with the protrusions 126, the contact area between adjacent microstructured antimicrobial films 100 in the antimicrobial film assembly 150 can be minimized. Minimizing the total contact area between adjacent microstructured antimicrobial films 100 can facilitate the removal or separation of an upper microstructured antimicrobial film 100 from a lower microstructured antimicrobial film 100 when necessary. In addition, in some embodiments, such as that of FIG. 3, the total contact area between the adhesive 119" of the bottom microstructured antimicrobial film 100 (the third microstructured antimicrobial film 100" in FIG. 3) of the antimicrobial film assembly 150 and the surface 160 is greater than the contact area between any of the adjacent microstructured antimicrobial films 100 in the antimicrobial film assembly 150. This configuration can facilitate the removal of a microstructured antimicrobial film 100 from the antimicrobial film assembly 150 without removing the antimicrobial film assembly 150 from the surface 160 to which the antimicrobial film assembly 150 is coupled, until desired.

Furthermore, as a result of the antimicrobial material 120 in each microstructured antimicrobial film 100 being recessed relative to the respective first major surface 108 (i.e., the upper surface 122 is spaced a distance from the first major surface 108), a stack of microstructured antimicrobial films 100 can be formed without contacting or disrupting the antimicrobial material 120 of one microstructured antimicrobial film 100 with the adhesive 119 of an adjacent microstructured antimicrobial film 100.

In addition, the adhesive 119 of the first microstructured antimicrobial film 100 can be coupled directly to the first major surface 108 of the second microstructured antimicrobial film 100', without the use of a release liner or a low adhesion backside (LAB) coating. By eliminating the need for release liners or LAB coatings, material and production costs can be reduced, and waste associated with disposal of release liners can be eliminated.

When the first microstructured antimicrobial film 100 has reached the end of its effective lifetime, the first microstructured antimicrobial film 100 can be peeled away from the remainder of the antimicrobial film assembly 150 (i.e., the second and third microstructured antimicrobial films 100' and 100") to expose the fresh second microstructured antimicrobial film 100', and so on.

In some embodiments, it can be advantageous to be able to remove one microstructured antimicrobial film 100 from the antimicrobial film assembly 150 at a time, without removing more than one, or without removing the antimicrobial film assembly 150 from the surface 160.

One way of accomplishing this is to configure the antimicrobial film assembly 150 such that the contact area between the adhesive 119 of one microstructured antimicrobial film 100 and the first major surface 108 of an adjacent microstructured antimicrobial film 100 generally increases toward the bottom of the antimicrobial film assembly 150. For example, instead of the antimicrobial film assembly 150 including multiple identical microstructured antimicrobial films 100, as shown in FIG. 3, the antimicrobial film assembly 150 can include a variety of microstructured antimicrobial films 100 in which the pitch (i.e., the center-to-center distance between adjacent wells 114) increases toward the bottom of the antimicrobial film assembly 150. For example, in such embodiments, the top microstructured antimicrobial film 100 would have the smallest average pitch, and the bottom microstructured antimicrobial film 100 would have the greatest average pitch. Another way to increase the contact area between adjacent microstructured antimicrobial films 100 toward the bottom of the antimicrobial film assembly 150 would be to provide an increasing number of protrusions 126 in the first major surface 108 of the microstructured antimicrobial films 100 toward the top of the antimicrobial film assembly 150. For example, instead of each of the microstructured antimicrobial films 100 including one protrusion 126 at each intersection of the walls 112, a microstructured antimicrobial film 100 positioned higher in the antimicrobial film assembly 150 can include more protrusions 126 in its first major surface 108 than a microstructured antimicrobial film 100 positioned lower in the antimicrobial film assembly 150.

Another way of accomplishing removal of one microstructured antimicrobial film 100 from the antimicrobial film assembly 150 at a time is to form the antimicrobial film assembly 150 from microstructured antimicrobial films 100 having different adhesives, such that a microstructured antimicrobial film 100 positioned lower in the antimicrobial film assembly 150 includes a more aggressive adhesive 119 than a microstructured antimicrobial film 100 positioned higher in the antimicrobial film assembly 150, and vice versa. Alternatively, the microstructured antimicrobial films 100 of the antimicrobial film assembly 150 can each include the same adhesive 119 but formed of different thicknesses, such that a microstructured antimicrobial film 100 positioned lower in the antimicrobial film assembly 150 includes a thicker adhesive 119 than a microstructured antimicrobial film 100 positioned higher in the antimicrobial film assembly 150, and vice versa. The term "more aggressive" is generally used with reference to adhesives to refer to an adhesive having a higher peel adhesion. For example, a more aggressive pressure sensitive adhesive can be an adhesive that has a higher peel adhesion than another adhesive according to ASTM D 3330, which is one standard for measuring the peel adhesion of pressure sensitive adhesives.

In the embodiment illustrated in FIG. 3, the antimicrobial film assembly 150 includes three identical microstructured antimicrobial films 100. However, as mentioned above, it should be understood that a variety of types of microstructured antimicrobial films can be employed in the antimicrobial film assembly 150, and that using different microstructured antimicrobial films can offer some advantages in some embodiments. The microstructured antimicrobial films of the antimicrobial film assembly 150 can be arranged regularly (e.g., alternating between the microstructured antimicrobial film 100 of FIGS. 1 and 2 and the microstructured antimicrobial film 200 of FIGS. 4 and 5, described below), randomly, or a combination thereof.

Figure 4:
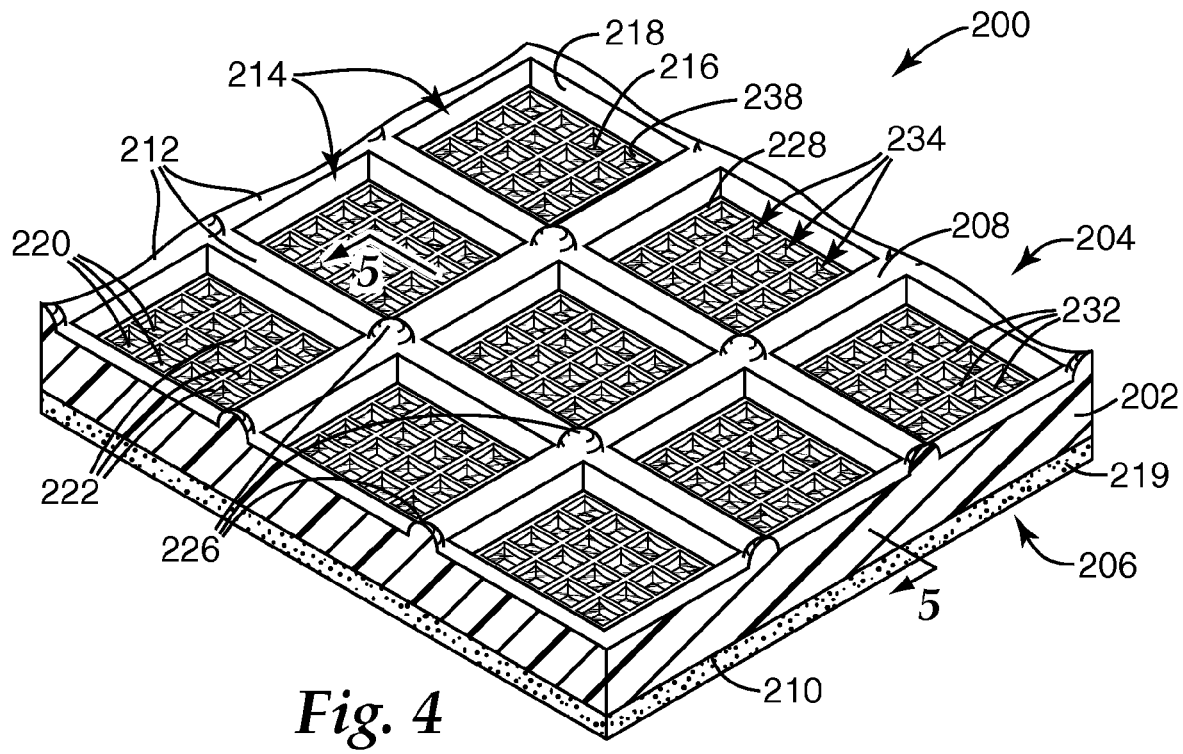
FIG. 4 is a schematic partial perspective view of a microstructured antimicrobial film according to another embodiment of the present disclosure.
Figure 5:
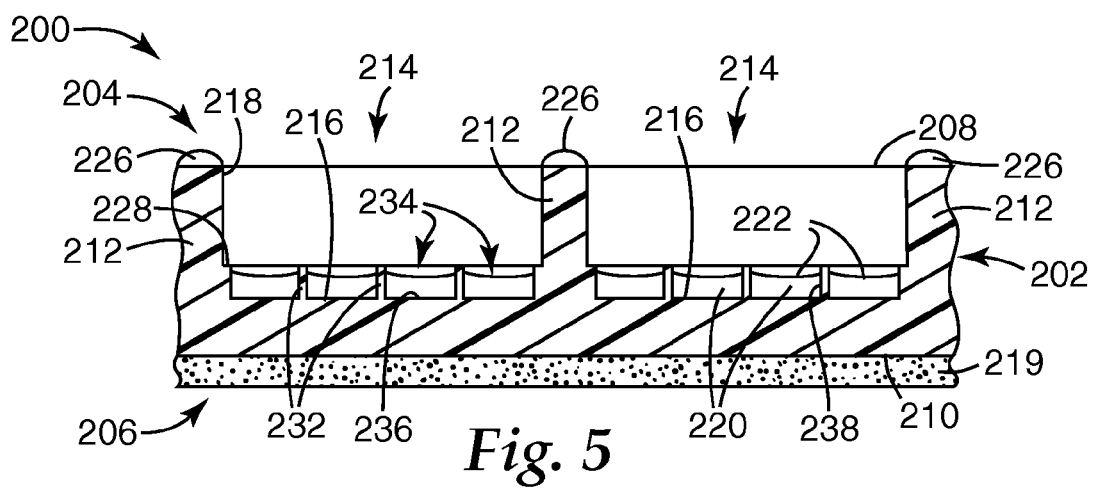
FIG. 5 is a schematic cross-sectional side view of the microstructured antimicrobial film of FIG. 4, taken along line 5-5 in FIG. 4.

FIGS. 4 and 5 illustrate a microstructured antimicrobial film 200 according to another embodiment of the present disclosure. The microstructured antimicrobial film 200 shares many of the same elements and features described above with reference to the illustrated embodiment of FIGS. 1 and 2. Accordingly, elements and features corresponding to the elements and features of the illustrated embodiment of FIGS. 1 and 2 are provided with the same reference numerals in the 200 series. Reference is made to the description above accompanying FIGS. 1 and 2 for a more complete description of the features and elements (and alternatives to such features and elements) of the embodiment illustrated in FIGS. 4 and 5.

The microstructured antimicrobial film 200 includes a substrate 202 having a first microstructured side 204 and a second side 206. The first side 204 of the substrate 202 includes a first major surface 208, and the second side 206 of the substrate 202 includes second major surface 210. The first major surface 208 is defined at least partially by a plurality of primary intersecting walls 212, and particularly, by an upper surface of the plurality of primary intersecting walls 212. The first major surface 208 can also be referred to as the "primary microstructured surface" 208. The primary microstructured surface 208 is further defined by a plurality of protrusions 226. The microstructured antimicrobial film 200 further includes an adhesive 219 coupled to the second major surface 210 on the second side 206 of the substrate 202.

The first side 204 of the substrate 202 further includes a plurality of primary wells 214 that are each defined at least partially by four primary walls 212 and a primary base 216. The primary base 216 is spaced a distance from the first major surface 208 of the substrate 202, such that the primary wells 214 are recessed in the first side 204 of the substrate 202. The primary walls 212 and the primary base 216 at least partially define a primary inner surface 218 of one primary well 214, and the primary inner surface 218 of the well 214 extends inwardly from the first major surface 208 of the substrate 202.

The microstructured antimicrobial film 200 further includes a second level or degree of microstructures. Particularly, the microstructured antimicrobial film 200 includes a secondary first major surface 228, which can also be referred to as a "secondary microstructured surface" 228. The secondary microstructured surface 228 is defined at least partially by a plurality of secondary intersecting walls 232, and particularly, by an upper surface of the plurality of secondary intersecting walls 232. The secondary microstructured surface 228 can further be defined by a plurality of secondary protrusions (or other microstructured features), which, for clarity, are not shown in FIGS. 4 and 5. In the embodiment illustrated in FIGS. 4 and 5, the upper surfaces of the plurality of secondary walls 232 are spaced a distance from the first major surface 208, such that the secondary walls 232 are recessed relative to the first major surface 208 of the microstructured antimicrobial film 200.

The secondary microstructured surface 228 is further defined by a plurality of secondary wells 234 that are each at least partially defined by four secondary walls 232 and a secondary base 236. The secondary base 236 is spaced a distance from the primary microstructured surface 208, and is spaced a distance from the secondary microstructured surface 228. The secondary walls 232 and the secondary base 236 at least partially define a secondary inner surface 238 of one secondary well 234, and the secondary inner surface 238 of the well 234 extends inwardly from the primary microstructured surface 208 and the secondary microstructured surface 228 of the substrate 202.

In the embodiment illustrated in FIGS. 4 and 5, the primary bases 216 are each at least partially defined by the plurality of secondary bases 236, and the secondary bases 236 are positioned the same distance from the primary microstructured surface 208 as the primary bases 216. However, it should be understood that the secondary bases 236 need not be positioned at the same depth as the primary bases 216, but rather, the secondary bases 236 can be positioned an additional distance from the primary microstructured surface 208 and can be spaced a distance from the respective primary base 216 as well. For example, in some embodiments, one or more of the primary wells 214 can include one or more secondary wells 234 positioned such that secondary well(s) 234 define a stepped configuration between the primary base 216 and the secondary base 236.

As shown in FIGS. 4 and 5, an antimicrobial material 220 can be positioned in the microstructured wells of the microstructured antimicrobial film 200, and particularly, in the secondary wells 234. That is, each primary well 214 and each secondary well 234 is adapted to retain the antimicrobial material 220. The antimicrobial material 220 includes an upper surface 222. In some embodiments, as shown in FIGS. 1 and 2, the antimicrobial material 220 is positioned in the secondary wells 234, such that the antimicrobial material 220 partially fills one or more of the secondary wells 234, and the upper surface 222 of the antimicrobial material 220 is spaced a distance from the secondary microstructured surface 228 and the primary microstructured surface 208 of the substrate 202. As a result, the antimicrobial material 220 is recessed in the first side 204 of the substrate 202, and further recessed from the secondary microstructured surface 228.

In the embodiment illustrated in FIGS. 4 and 5, the secondary walls 232 are illustrated as being shorter than the primary walls 212; however, it should be understood that the secondary walls 232 can instead be as tall as (or more similarly sized relative to) the primary walls 212. In embodiments employing shorter secondary walls 232, the antimicrobial material 220 can be allowed to overfill the secondary wells 234 and still be retained in a recessed configuration relative to the primary microstructured surface 208 (i.e., the upper surface 222 of the antimicrobial material 220 can still be spaced a distance from the primary microstructured surface 208).

The embodiment illustrated in FIGS. 4 and 5 includes two levels or degrees of microstructuring by way of example only. However, additional degrees of microstructuring in the first side 204 of the substrate 202 can further enhance the retention of the antimicrobial material 220 in the microstructured antimicrobial film 200. Such additional degrees of microstructuring can include additional tertiary microstructures, quaternary microstructures, and so on. Each additional level of microstructuring can go increasingly deeper into the substrate 202, the additional wells formed can have bases spaced the same distance from the primary microstructured surface 208 as the primary bases 216, or a combination thereof.

The microstructured antimicrobial film 200 of FIGS. 4 and 5 shows primary wells 214, and a plurality of secondary wells 234 in each of the primary wells 214. However, it should be understood that a variety of regular configurations, random configurations, or combination configurations are possible. For example, in some embodiments, random primary wells 214 can include secondary wells 234, or every other primary well 214 can include secondary wells 234, or some regions of the microstructured antimicrobial film 200 can include primary and secondary wells 214 and 234, while some regions of the microstructured antimicrobial film 200 include only primary wells 214, etc.

In the embodiment illustrated in FIGS. 4 and 5, the secondary walls 232 are oriented substantially parallel or perpendicular with respect to the primary walls 212. However, it should be understood that the secondary walls 232 can instead be oriented at a variety of other angles (e.g., 45 degrees) with respect to the primary walls 212. In addition, the secondary wells 234 are illustrated as having the same shape as that of the primary wells 214; however, it should be understood that all of the alternatives described above with respect to the wells 114 of FIGS. 1 and 2 regarding shape, number, orientation, size, etc. apply to the primary wells 214 and the secondary wells 234 of the microstructured antimicrobial film 200 of FIGS. 4 and 5.

For example, the microstructured antimicrobial film 200 illustrated in FIGS. 4 and 5 is shown as having sixteen secondary wells 234 formed in each primary well 214. However, the microstructured antimicrobial film 200 can include as few as zero secondary wells 234, and as many as possible and desired per primary well 214.

The secondary walls 232 and wells 234 can range in size and can be defined by the size ranges given above with respect to the walls 112 and wells 114 of FIGS. 1 and 2. Furthermore, in some embodiments, the secondary wells 234 can have an average depth or the secondary walls 232 can have an average height of at least about 0.1 micrometers, in some embodiments, at least about 1 micrometers, and in some embodiments, at least about 2 micrometers. In some embodiments, the secondary wells 234 can have an average depth or the secondary walls 232 can have an average height of no greater than about 50 micrometers, in some embodiments, no greater than about 20 micrometers, in some embodiments, no greater than about 10 micrometers, and in some embodiments, no greater than about 5 micrometers.

The secondary walls 232 and wells 234 can be further defined by their relative sizes, as compared to the primary walls 212 and wells 214. For example, in some embodiments, the average secondary wall height or the average secondary well depth is at least about 5 micrometers less than the average primary wall height or the average primary well depth, respectively. The average primary wall height and the average primary well depth, along with the other characteristics of the primary walls 212 and wells 214 can be assumed to be the same as those described above with respect to the walls 112 and wells 114 of FIGS. 1 and 2. Furthermore, in some embodiments, the average secondary wall height or the average secondary well depth is at least about 20 micrometers less than the average primary wall height or the average primary well depth, respectively, in some embodiments, at least about 50 micrometers less, and in some embodiments, at least about 70 micrometers less.

In some embodiments, the ratio of the average primary well volume to the average secondary well volume is at least about 5, in some embodiments, at least about 30, in some embodiments, at least about 50, and in some embodiments, at least about 150. In some embodiments, the ratio of the average primary well volume to the average secondary well volume is no greater than about 2,000,000, in some embodiments, no greater than about 1,000,000, in some embodiments, no greater than about 150,000, and in some embodiments, no greater than about 500.

Figure 6:
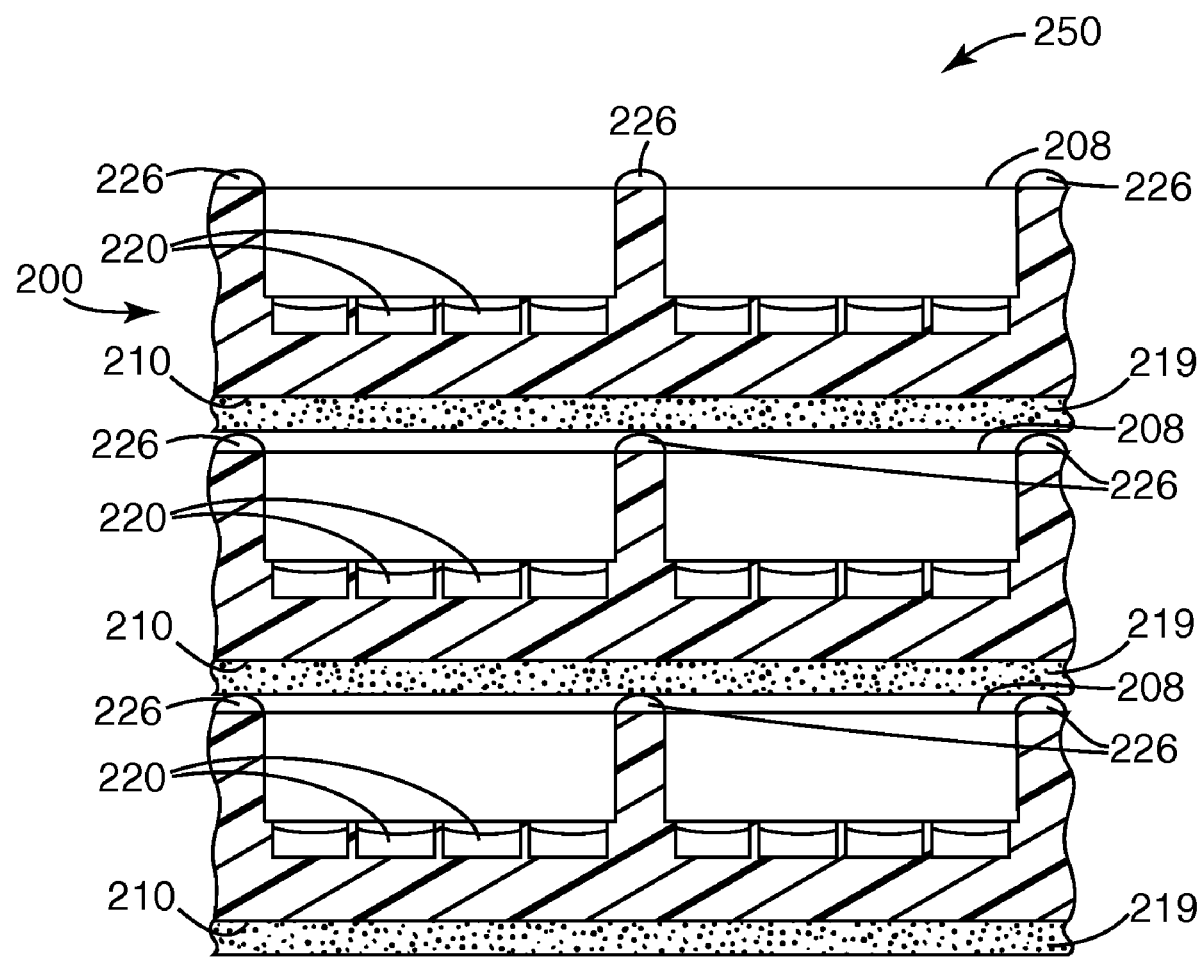
FIG. 6 is a schematic cross-sectional side view of an antimicrobial film assembly according to another embodiment of the present disclosure, the antimicrobial film assembly comprising the microstructured antimicrobial film of FIGS. 4 and 5.

FIG. 6 illustrates an antimicrobial film assembly 250 that includes a rolled form of the microstructured antimicrobial film 200 of FIGS. 4 and 5. Particularly, FIG. 6 illustrates a section of a roll formed by winding the microstructured antimicrobial film 200 upon itself. As shown in FIG. 6, no release liner or LAB coating is necessary in order to wind the microstructured antimicrobial film 200 upon itself. In addition, the protrusions 226 of the first major surface 208 of one portion of the microstructured antimicrobial film 200 contact the adhesive 219 (which is coupled to the second major surface 210) of another portion of the microstructured antimicrobial film 200 to minimize the contact area between adjacent portions of the microstructured antimicrobial film 200. Furthermore, the antimicrobial material 220 in one portion of the microstructured antimicrobial film 200 is at least partially covered by another portion of the microstructured antimicrobial film 200, with the exception of the outermost layer of the antimicrobial film assembly 250.

In the embodiment illustrated in FIG. 6, the entire antimicrobial film assembly 250 is comprised of one microstructured antimicrobial film 200. However, in some embodiments, the antimicrobial film assembly 250 can include a roll formed of a variety of types of microstructured antimicrobial films. For example, in some embodiments, a first microstructured antimicrobial film (e.g., the microstructured antimicrobial film 100 of FIGS. 1 and 2) can be wound upon itself to form a first roll, and then a second microstructured antimicrobial film (e.g., the microstructured antimicrobial film 200 of the FIGS. 4 and 5) can be wound around the first roll, and so on.

The antimicrobial film assembly 250 is shown in FIG. 6 as a roll by way of example only. However, it should be understood that the microstructured antimicrobial film 200 can instead be employed in a stack, similar to the antimicrobial film assembly 150 described above. Such an antimicrobial film assembly can include a plurality of microstructured antimicrobial films 200, or a combination of microstructured antimicrobial films. In addition, such a stack can employ any of the alternatives described above with respect to the antimicrobial film assembly 150 of FIG. 3.

In addition, if necessary to facilitate the removal of the first layers of microstructured antimicrobial film 200 from the antimicrobial film assembly 250, some of the techniques described above with respect to FIG. 3 can be employed to make it easier to peel off the microstructured antimicrobial film 200 from the antimicrobial film assembly 250 at the beginning of the roll than at the end (i.e., center) of the roll, such that it becomes more difficult to unwind the microstructured antimicrobial film 200 toward the center of the roll (i.e., toward the bottom of antimicrobial film assembly 250 illustrated in FIG. 6).

The following working examples are intended to be illustrative of the present disclosure and not limiting.

EXAMPLES

The present disclosure is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques. Unless otherwise noted, materials were obtained from Sigma Aldrich Chemical Co., St. Louis, Mo.

The following compositional abbreviations are used in the following Examples:

| | |
|---|---|
| "AgION": | A silver-containing inorganic zeolite food-grade antimicrobial agent, type AJ, which contains 2.5% silver, and which is commercially available under the trade designation "AgION" Antimicrobial from AgION Technologies, Inc., Wakefield, MA. |
| "Permuthane": | Permuthane SU26-248 polyurethane in toluene (25% solids), commercially available from Stahl USA. |
| "N-75 isocyanate": | A 75% 1,6-hexamethylene diisocyanate in butyl acetate and xylene, Bayer N75BA/X, commercially available from Bayer Polymers LLC, Pittsburgh, PA. |
| "GLAM film": | A POST-IT ™ self-stick bulletin board (Cat #558G, available from 3M Company, St. Paul, MN) having a microsphere adhesive surface. |
| "Triclosan": | Triclosan antimicrobial agent, commercially available from Ciba Specialty Chemicals., Tarrytown, NY. |
| "Lauricidin": | A glycerol monolaurate fatty acid monoester, commercially available under the trade designation "LAURICIDIN," commercially available from Med-Chem Laboratories, East Lansing, MI. |
| "DOSS surfactant": | A dioctylsulfosuccinate (DOSS) surfactant, commercially available from Alfa Aesar, Ward Hill, Mass. |

-continued

| | |
|---|---|
| "Salicylic acid": | A 2-hydroxybenzoic acid ($HOC_6H_8CO_2H$) with a formula weight of 138.1, commercially available from Sigma-Aldrich Chemical Company, St. Louis, MO. |
| "Neocryl XK-90": | A water based acrylic emulsion comprising 40% cross-linkable acrylic emulsion, commercially available from DSM NeoResins, Wilmington, MA |
| "CX-100": | An aziridine cross-linker commercially available under the trade designation "CX-100" from DSM NeoResins, Wilmington, MA. |
| "Surfynol 104PA": | A nonionic surfactant comprising 50% active liquid in 2-ethylhexanol, commercially available from Air Products and Chemicals, Inc., Allentown, PA. |
| "Myacide AS": | An antimicrobial agent commercially available under the trade designation "MYACIDE AS" from BASF Corp., Parsippany, NJ. |
| "Bardac 208M": | A quaternary ammonium compound commercially available under the trade designation "BARDAC 208M" from Lonza Group Ltd., Valais, Switzerland. |

Microstructured Film

Figure 7:
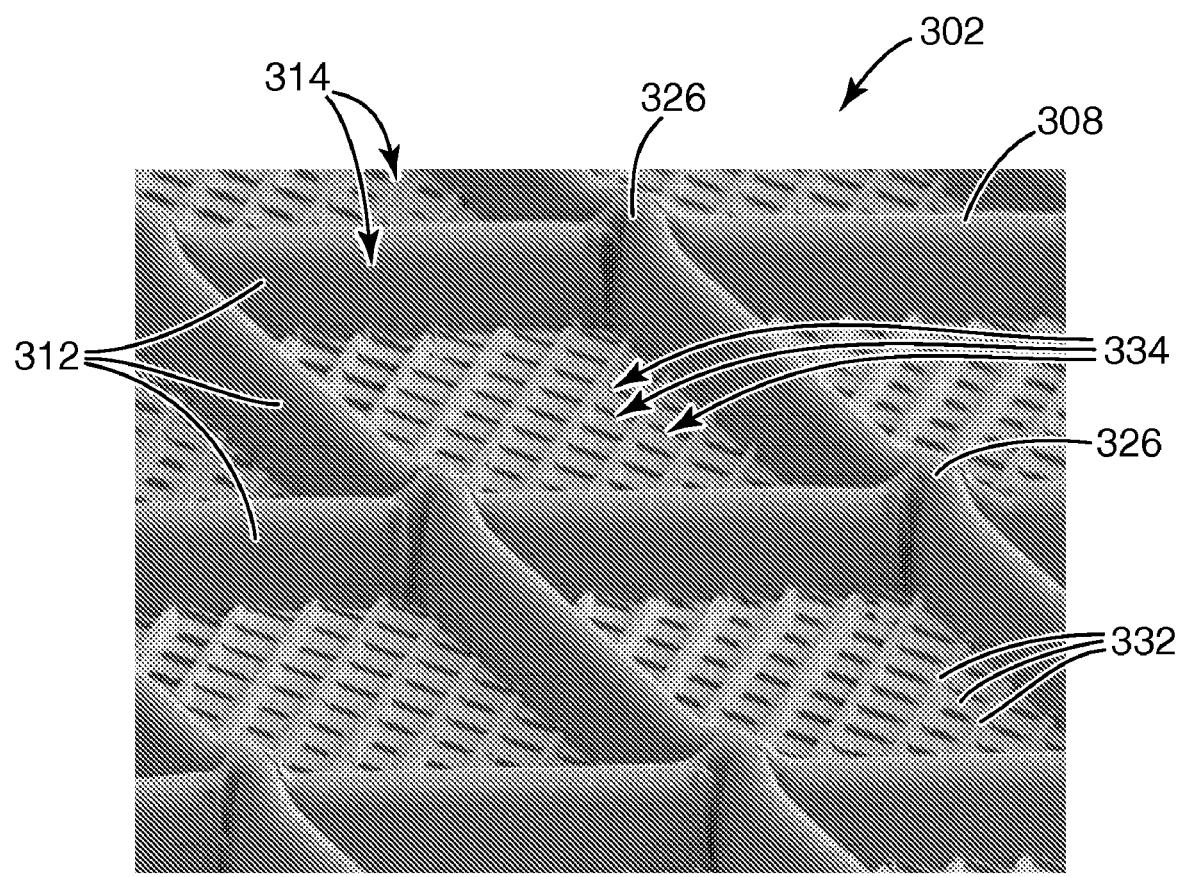
FIG. 7 is an optical micrograph of a microstructured film used in the Examples.

A polypropylene microstructured film/substrate 302 with a microstructured surface 308 was produced by casting molten polypropylene resin against a cast roll with the inverse of the desired film pattern. A scanning electron micrograph of the microstructured film 302 is shown in FIG. 7. Additional details of the microstructured film used are described in Halverson et al., PCT Publication No. WO 2007/070310. The microstructured surface 308 of the film 302 comprised primary wells 314 separated by primary walls 312. The primary walls 312 and the primary wells 314 included a pitch (i.e., a center to center spacing between adjacent primary walls 312 or wells 314, respectively) of about 250 micrometers. The wells 314 were rhomboidal in shape with a nominal depth of about 67 micrometers, and the walls 312 were oriented at a 45 degree angle with respect to the machine direction of the film 302. Inspection with a Wyko Interferometer microscope (Model RST, from Veeco Metrology Group, Tucson, Ariz.) revealed a plurality of upwardly-directed protrusions 326 positioned at the intersections of the primary walls 312. The wall height between the intersections was about 67 micrometers, and the wall height in the region of the intersections of the walls was about 75 micrometers. As a result, the protrusions 326 each measured about 8 micrometers in height. The microstructured film 302 further included secondary walls 332 that sub-divided each of the primary wells 314 into secondary wells 334. The secondary walls 332 were about 4 micrometers in height, and the secondary walls 332 and the secondary wells 334 included a pitch (i.e., a center to center distance between adjacent secondary walls 332 or wells 334, respectively) of about 25 micrometers. The secondary walls 332 were arranged such that they were either parallel or perpendicular to the machine direction of the film 302 (i.e., the secondary walls 332 were arranged at an angle of about 45 degrees with respect to the primary walls 312).

Test Methods

Zone of Inhibition Assay Method

*S. aureus* (ATCC 6538) (American Type Culture Collection, Manassas, Va.), gram positive (+) testing, and *P. aeruginosa* (ATTC 9027), gram negative (−) testing.

An inoculum suspension was prepared that contained a concentration of approximately $1\times10^8$ colony forming units (CFU) per milliliter (mL) in Phosphate Buffered Saline (PBS) obtained from EMD Biosciences of Darmstadt, Germany, using a 0.5 McFarland Equivalence Turbidity Standard. A bacterial lawn was prepared by dipping a sterile cotton applicator into the suspension and swabbing the dry surface of a trypticase soy agar (TSA) plate in three different directions. Three 7-mm disks of each film were prepared, placed active (i.e., antimicrobial-coated) side down on the inoculated plate, and pressed firmly against the agar with sterile forceps to ensure complete contact with the agar. The plates were incubated at 4° C. for 3 hours and then incubated at 36° C.+/−1° C. for 24 hours. The area under and surrounding the samples was examined for bacterial growth. The reported results were the average values of the diameter of the circles surrounding each sample where no growth was observed. For example, a zone of 7 indicates that no growth was observed underneath the 7 mm disk, and a zone of 9 indicates that no growth was observed underneath the 7 mm disk, as well as in an area surrounding the disk, where the total diameter of the no growth area (i.e., including the area under the disk) was 9 mm.

Microbial Load Reduction Assay Method

The "microbial load reduction" was tested pursuant to ASTM E2180-01 (Approved Dec. 10, 2001; published February, 2002), which involved inoculation of a molten (45° C.) agar slurry with a standardized culture of bacterial cells. A thin layer of the inoculated agar slurry (0.5 milliliter) was then pipetted onto the test material and the untreated control material. Samples were tested in duplicate using *S. aureus* (ATCC 6538) and *P. aeruginosa* (ATCC 9027). After 24 hours, surviving microorganisms were recovered via elution of the agar slurry inoculum from the test substrate into D/E Neutralizing broth and extracted by sonication and vortexing. Serial dilutions were then made, and pour plates were made of each dilution. Agar plates were incubated for 48 hours at 28° C.±1° C. Bacterial colonies from each dilution series were then counted and recorded. Calculation of percent reduction of bacteria from treated versus untreated samples was then made. Reported results are typically the average of two replicates per sample.

Example 1

An antimicrobial composition comprising 20 parts Permuthane, 30 parts toluene, 2 parts N-75 isocyanate, and 0.2 parts AgION was prepared by mixing all ingredients in a small jar. The antimicrobial composition was applied onto the microstructured side of the microstructured film using a smooth Teflon coated glass rod to force the coating into the primary wells of the film below the first major surface of the film, so that when the solvent evaporated, the binder/antimicrobial composition was confined within the primary wells of microstructured surface of the film, below the first major surface of the film, to form a microstructured antimicrobial film.

The antimicrobial coated surface of the microstructured antimicrobial film was contacted with the adhesive surface of GLAM film, and the construction was rolled twice with a 1300 gram roller.

The construction was aged for 54 days at 73.4° F. (23° C.) and 50% Relative Humidity. Three one-inch-wide pieces of the construction were formed and the 90° peel adhesion of each were measured. The average of the three measurements was 13.4 grams/inch and the standard deviation of the measurements was 0.6 grams/inch. After removing the GLAM film, the antimicrobial activity of the microstructured film was determined according to the microbial load reduction assay method. Microbial load reduction results before and after adhesive contact are given in Table 1 below.

TABLE 1

Microbial load reduction results.

| Sample | % Reduction in *S. aureus* (Gram positive) | % Reduction in *P. aeruginosa* (Gram negative) |
|---|---|---|
| Before adhesive contact | 88.1% | 99.99% |
| After adhesive contact | 88.5% | 100% |

The data show that aging the microstructured antimicrobial film against an adhesive did not affect its antimicrobial properties. Antimicrobial performance against *S. aureus* could be improved by increasing the amount of antimicrobial added (this sample contained 0.025% silver), or by blending into the coating a synergistic antimicrobial such as Triclosan or a quaternary amine compound.

Example 2

A fatty acid monoester-based antimicrobial material comprising: 20 wt % Lauricidin, 10 wt % Salicylic acid, 10 wt % Doss surfactant (50% solution), and 60 wt % isopropyl alcohol was brush coated onto the microstructured side of the microstructured film using a smooth Teflon-coated glass rod in order to force the antimicrobial material into the primary wells of the microstructured film to form a microstructured antimicrobial film. As a control, the same antimicrobial material was coated onto the smooth side (i.e., the second side) of the microstructured film using Meier rod #24 providing for a dry coating thickness of about 8 micrometers. The coatings were allowed to dry in an oven at 50° C. for 5 minutes. Zone of inhibition testing and microbial load reduction testing were performed on both samples. The results are shown in Tables 2 and 3 below.

TABLE 2

Zone of inhibition results.

| | *S. aureus* (Gram positive) | | *P. aeruginosa* (Gram negative) | |
|---|---|---|---|---|
| Sample | Zone of Inhibition (mm) | Growth Under the Sample | Zone of Inhibition (mm) | Growth Under the Sample |
| PP film (control) | None | Moderate growth | None | Moderate growth |
| Antimicrobial Material on smooth PP film | 12 | No growth | 0 | No growth |
| Antimicrobial Material on microstructured PP film | 15 | No growth | 0 | No growth |

TABLE 3

Microbial load reduction results. (The number in parentheses indicates the recovered bacteria reported in colony forming units (CFU) per square cm (cm$^2$).)

| Sample | % Reduction in *S. aureus* (Gram positive) | % Reduction in *P. aeruginosa* (Gram negative) |
|---|---|---|
| Antimicrobial Material on PP film | 100% (<3.1 CFU/cm$^2$) | 100% (<3.1 CFU/cm$^2$) |
| Antimicrobial Material on microstructured PP film | 100% (<3.1 CFU/cm$^2$) | 100% (<3.1 CFU/cm$^2$) |

Example 3

An acrylic binder-based antimicrobial material was prepared by mixing 9 parts Neocryl XK-90 with 1 part crosslinker part B. Part B was made by combining 76 parts ethyl alcohol, 22.8 parts CX-100, and 1.2 parts Surfynol 104PA. All ingredients were combined in a beaker and mixed for 20 minutes under high shear. To this mixture 0.5 part AgION was added. The final composition was coated onto the microstructured side of the microstructured film using a smooth Teflon-coated glass rod in order to force the coating into the primary wells of the microstructured film to form a microstructured antimicrobial film. As a control, the same acrylic based antimicrobial material was coated onto the smooth side (i.e., the second side) of the microstructured film using a Meier rod #24 providing for a dry coating thickness of about 10 micrometers. Both coated samples were dried in a 55° C. oven for 10 minutes and tested using the microbial load reduction assay method. Microbial load reduction results are given in Table 4.

TABLE 4

Microbial load reduction results. (The number in parentheses indicates the recovered bacteria reported in colony forming units (CFU) per square cm (cm$^2$).)

| Sample | % Reduction in *S. aureus* (Gram positive) | % Reduction in *P. aeruginosa* (Gram negative) |
|---|---|---|
| PP film | 99.9% (6.22 × 10$^2$ CFU/cm$^2$) | 100% (7.75 CFU/cm$^2$) |
| Microstructured PP film | 99.8% (1.14 × 10$^3$ CFU/cm$^2$) | 100% (6.98 CFU/cm$^2$) |

Example 4

Two antimicrobial materials were formed: (1) a 20% solution of Myacide AS in isopropyl alcohol, and (2) a 50% solution of Bardac 208M in isopropyl alcohol. A smooth Teflon-coated glass rod was used to coat each antimicrobial material onto the microstructured side of a microstructured film to form two microstructured antimicrobial films. As a control, the same antimicrobial materials were each coated onto the smooth side (i.e., the second side) of a microstructured film using a Meier Rod #24 providing for a wet coating thickness of about 24 micrometers. The microstructured antimicrobial films and the control coated films were dried in an oven at 60° C. for 5 minutes. The control coated films felt greasy to the touch, and the antimicrobial material could be removed by wiping with the finger, while the coated microstructured side of the microstructured antimicrobial films did not appear or feel greasy, and the antimicrobial material could not be wiped off. Microbial load reduction results of the four samples using ASTM E2180-01 test method are given in Table 5.

TABLE 5

Microbial load reduction results. (The number in parentheses indicates the recovered bacteria reported in colony forming units (CFU) per square cm (cm$^2$).)

| Sample | % Reduction in *S. aureus* (Gram positive) | % Reduction in *P. aeruginosa* (Gram negative) |
|---|---|---|
| PP film with Myacide (control) | 100 (<3.1 CFU/cm$^2$) | 100 (<3.1 CFU/cm$^2$) |
| Microstructured PP film with Myacide | 100 (<3.1 CFU/cm$^2$) | 100 (15 CFU/cm$^2$) |
| PP film with Bardac (control) | 100 (<3.1 CFU/cm$^2$) | 100 (<3.1 CFU/cm$^2$) |
| Microstructured PP film with Bardac | 100 (<3.1 CFU/cm$^2$) | 100 (<3.1 CFU/cm$^2$) |

The embodiments described above and illustrated in the figures are presented by way of example only and are not intended as a limitation upon the concepts and principles of the present invention. As such, it will be appreciated by one having ordinary skill in the art that various changes in the materials, elements, and their configuration and arrangement are possible without departing from the spirit and scope of the present invention. Various features and aspects of the present invention are set forth in the following claims.

What is claimed is:

1. A microstructured antimicrobial film comprising:
   a substrate having a first side, the first side including a first major surface;
   a plurality of microstructured wells defined in the first side of the substrate, each of the plurality of wells at least partially defined by a base, the base being spaced a distance from the first major surface of the substrate, wherein each of the plurality of wells has at least one dimension in the plane of the first major surface, and wherein the at least one dimension is less than 1000 micrometers; and
   an antimicrobial material positioned within at least some of the plurality of wells, such that the antimicrobial material has an upper surface that is spaced a distance from the first major surface of the substrate and is recessed in the first side of the substrate, and such that the antimicrobial material is contained within the at least some of the plurality of wells and the first major surface is free of the antimicrobial material.

2. The microstructured antimicrobial film of claim 1, wherein the base of each of the plurality of wells is spaced less than 250 micrometers from the first major surface.

3. The microstructured antimicrobial film of claim 1, wherein the substrate comprises at least one of a polyester, a polyolefin, a polyacrylate, a biodegradable polymer, a polyvinyl chloride, and a combination thereof.

4. The microstructured antimicrobial film of claim 1, wherein the substrate comprises at least one of a polyethylene terephthalate, a polyethylene, a polypropylene, a polymethyl methacrylate, a cellulose derivative, a polyglycolic acid, a polylactic acid, a polyvinyl chloride, and a combination thereof.

5. The microstructured antimicrobial film of claim 1, wherein the antimicrobial material comprises at least one of chlorhexidine gluconate (CHG), parachlorometaxylenol (PCMX), a fatty acid monoester/monoether, a quaternary ammonium compound, a polyhexamethylene biguanide, a silver-containing compound, and combinations thereof.

6. The microstructured antimicrobial film of claim 1, wherein the antimicrobial material comprises a liquid.

7. The microstructured antimicrobial film of claim 1, wherein the antimicrobial material comprises a flowable powder.

8. The microstructured antimicrobial film of claim 1, wherein the antimicrobial material comprises an antimicrobial agent dispersed in a polymer binder.

9. The microstructured antimicrobial film of claim 1, wherein the plurality of wells is a primary plurality of wells, the plurality of intersecting walls is a plurality of primary intersecting walls, and the base of each of the plurality of wells is a primary base, and wherein each of the primary plurality of wells further comprises a secondary plurality of wells, wherein each of the secondary plurality of wells is at least partially defined by a secondary base that is spaced a distance from the first major surface of the substrate.

10. The microstructured antimicrobial film of claim 9, wherein the secondary base forms a portion of the primary base and is spaced the same distance from the first major surface that the primary base is spaced.

11. The microstructured antimicrobial film of claim 9, wherein the secondary base is further recessed from the primary base.

12. The microstructured antimicrobial film of claim 9, wherein the first major surface is a primary microstructured surface, wherein the secondary wells are formed in a secondary microstructured surface, and wherein the antimicrobial material is positioned within the plurality of secondary wells, such that the upper surface of the antimicrobial material is spaced a distance from the secondary microstructured surface.

13. A microstructured antimicrobial film comprising:
a substrate having a first side, the first side including a first major surface at least partially defined by the upper surfaces of a plurality of intersecting walls;
a plurality of microstructured wells defined in the first side of the substrate, each of the plurality of wells at least partially defined by a base and at least three of the plurality of intersecting walls, the base being spaced a distance from the first major surface of the substrate, wherein each of the plurality of wells has at least one dimension in the plane of the first major surface, and wherein the at least one dimension is less than 1000 micrometers; and
an antimicrobial material positioned within at least some of the plurality of wells, such that the antimicrobial material has an upper surface that is spaced a distance from the first major surface of the substrate and is recessed in the first side of the substrate, and such that the antimicrobial material is contained within the at least some of the plurality of wells and the first major surface is free of the antimicrobial material.

14. The microstructured antimicrobial film of claim 13, wherein the plurality of wells is a primary plurality of wells, the plurality of intersecting walls is a plurality of primary intersecting walls, and the base of each of the plurality of wells is a primary base, and wherein each of the primary plurality of wells further comprises a secondary plurality of wells, wherein each of the secondary plurality of wells is at least partially defined by a secondary base and at least one secondary wall.

15. The microstructured antimicrobial film of claim 14, wherein the secondary base forms a portion of the primary base and is spaced the same distance from the first major surface that the primary base is spaced.

16. The microstructured antimicrobial film of claim 14, wherein the at least one secondary wall is shorter than the plurality of primary intersecting walls, such that the upper surface of the at least one secondary wall is spaced a distance from the first major surface of the substrate.

17. The microstructured antimicrobial film of claim 14, wherein the antimicrobial material is positioned within the plurality of secondary wells, such that the upper surface of the antimicrobial material is spaced a distance from the upper surface of the at least one secondary wall.

18. The microstructured antimicrobial film of claim 14, wherein the at least one secondary wall is oriented at an angle of about 45 degrees with respect to the plurality of primary intersecting walls.

19. An antimicrobial film assembly comprising:
a first antimicrobial film and a second antimicrobial film, each of the first antimicrobial film and the second antimicrobial film comprising
a substrate having a first side having a first major surface and a second side having a second major surface,
a plurality of microstructured wells defined in the first side of the substrate, the plurality of wells recessed from the first major surface of the substrate, and
an antimicrobial material positioned within the plurality of wells,
the first antimicrobial film further comprising an adhesive coupled to the second major surface of the substrate, the adhesive of the first antimicrobial film positioned in contact with the first major surface of the second antimicrobial film such that the first antimicrobial film and the second antimicrobial film form a stack.

\* \* \* \* \*

UNITED STATES PATENT AND TRADEMARK OFFICE
CERTIFICATE OF CORRECTION

PATENT NO. : 8,318,282 B2  
APPLICATION NO. : 12/746792  
DATED : November 27, 2012  
INVENTOR(S) : Caroline M. Ylitalo et al.

Page 1 of 1

It is certified that error appears in the above-identified patent and that said Letters Patent is hereby corrected as shown below:

Column 15  
Line 27, Delete "antimicrobical" and insert -- antimicrobial --, therefor.  
Line 36, Delete "triodide)" and insert -- triiodide) --, therefor.

Column 16  
Line 10, Delete "octenidenes;" and insert -- octenidines; --, therefor.  
Line 20, Delete "napthenate)," and insert -- naphthenate), --, therefor.  
Line 46, Delete "Uniquema" and insert -- Uniqema --, therefor.  
Line 55, Delete "monethers," and insert -- monoethers, --, therefor.

Column 18  
Line 25, Delete "(Pittsburg," and insert -- (Pittsburgh, --, therefor.

Column 30  
Line 8, Delete "MA" and insert -- MA. --, therefor.  
Line 59, Delete "(ATTC" and insert -- (ATCC --, therefor.

Signed and Sealed this  
Second Day of April, 2013

Teresa Stanek Rea  
*Acting Director of the United States Patent and Trademark Office*